(12) United States Patent
Thornthwaite

(10) Patent No.: US 8,247,435 B2
(45) Date of Patent: Aug. 21, 2012

(54) FORMULATIONS FOR TREATING HUMAN AND ANIMAL DISEASES

(76) Inventor: Jerry T. Thornthwaite, Henderson, TN (US)

( * ) Notice: Subject to any disclaimer, the term of this patent is extended or adjusted under 35 U.S.C. 154(b) by 453 days.

(21) Appl. No.: 12/388,674

(22) Filed: Feb. 19, 2009

(65) Prior Publication Data
US 2010/0209497 A1 Aug. 19, 2010

(51) Int. Cl.
*A23L 1/302* (2006.01)
*A23L 1/305* (2006.01)
*A61K 31/56* (2006.01)
*A61K 31/195* (2006.01)

(52) U.S. Cl. ........ 514/332; 514/456; 514/458; 514/171; 514/562; 514/494; 424/702; 424/615; 426/648

(58) Field of Classification Search .................. 514/332, 514/456, 458, 171, 562, 494; 424/702, 615
See application file for complete search history.

(56) References Cited

U.S. PATENT DOCUMENTS

| 5,972,382 | A | * | 10/1999 | Majeed et al. | 424/464 |
| 6,316,008 | B1 | * | 11/2001 | Godfrey | 424/400 |
| 6,664,272 | B2 | * | 12/2003 | Snyder et al. | 514/327 |
| 7,288,271 | B2 | * | 10/2007 | Graus et al. | 424/728 |
| 7,951,847 | B2 | * | 5/2011 | Kaiser | 424/641 |
| 2006/0020046 | A1 | * | 1/2006 | Goralczyk et al. | 514/763 |
| 2006/0078629 | A1 | * | 4/2006 | Serfontein | 424/702 |

FOREIGN PATENT DOCUMENTS
CN 1762236 A * 4/2006
* cited by examiner

*Primary Examiner* — Gina C Yu
(74) *Attorney, Agent, or Firm* — Bradley Arant Boult Cummings, LLP

(57) ABSTRACT

The present disclosure provides for a scientific formulation useful in the treatment and prevention of human and animal diseases. A biologically effective amount of each of the components of the formulation is administered to patients in pill (or capsule) form via multiple different and identifiable pills. The compounds of the formulation are segregated into different pill types, and contain various amounts of the compounds Curcumin, Genistein, Squalamine, Vitamin E, N-Acetyl-Cysteine, Methylselenocysteine, Zinc Gluconate, B Complex, Lentinen, Coenzyme Q10 Acetyl-L-Carnitine, Lipoic Acid, Resveratrol, and Vitamin C. Furthermore, Arabinoxylan and/or Peperine may be added to the various pill formulations.

11 Claims, No Drawings

FORMULATIONS FOR TREATING HUMAN AND ANIMAL DISEASES

FIELD OF THE INVENTION

The present disclosure relates generally to cancer treatment. In particular, the present disclosure relates to a scientific formulation for the treatment of cancer.

BACKGROUND OF THE INVENTION

There is general acceptance that treatment of cancer using surgery with or without radiotherapy remains the first treatment modality for most cancer protocols. Radiotherapy is used quite successfully for many forms of cancer while chemotherapy has become an integral part of a multi-disciplinary treatment of cancers and has served also as a palliative measure in cases of advanced cancer.

Despite advances in the early detection of tumors and in the use of surgery, radiation and chemical therapies for disease management, the worldwide mortality from human cancer remains unacceptably high and has increased in the last few years. In the United States from 1930 through 2004, a trend of increasing cancer deaths is shown among both men and women. Although advances in the early detection of tumors and in the use of chemotherapy and surgery for disease management have helped to enhance the overall survival of afflicted patients, major improvements in treatments for most human cancers are urgently needed.

The control and therapy of cancer may benefit from introduction of new treatments derived from natural products. Many pharmaceutical products approved for human disease treatment are derived from natural sources. The discovery of efficacious compounds for cancer management will benefit from new understandings of molecular and cellular pathways that regulate tumor proliferation and progression.

Patients are becoming acutely aware of the alternative approaches. Nine studies performed worldwide among cancer patients showed that 41.2% used complementary and alternative medicine during their treatment.

In almost all cases of treatment failure, the patient develops distant metastases. While surgery, radiotherapy and chemotherapy are all available to eradicate loco-regional disease, they are of little value with distant metastases. For such distant metastases, chemotherapy is the recommended approach, but effectiveness is limited by toxic side-effects at high doses and lack of specificity. Furthermore, within the holistic approach of clinical cancer therapy there is now increasing emphasis being given to patient quality of life following these classical treatments, which is encompassed in the term "hospice." The conclusion is survival should not be the sole criterion for assessing the treatment results. Thus, it has increasingly become an accepted practice for the oncologist to provide a way to make the patient "comfortable" during treatment.

It is also well-recognized that both radiotherapy and chemotherapy invariably damage or weaken the patient's immunological defenses which may have already been damaged by the cancer itself. From these observations there has now developed a new awareness in cancer therapy concerning the importance of the patient's immune system. Biological Response Modifiers (BRMs) have now evolved as the fourth method of cancer treatment in addition to surgery, radiotherapy and chemotherapy. Such treatments with BRMs are considered more biological than directly cytotoxic.

In the present disclosure, formulations are provided which are based on numerous references to key ingredients derived from natural sources in chemically pure form that have direct and safe efficacies in the treatment of cancer. The formulation can be considered a supplement to the current cancer treatment methods. However, the importance of the components of the formulation, such as antioxidants, antiangiogenic compounds, natural killer cell and other immune stimulators and direct cancer cytotoxicity, should be considered as a possible first line of treatment and prevention of cancer in the near future.

SUMMARY OF THE INVENTION

The present disclosure provides for formulations useful in the treatment of human and animal diseases. In particular, the formulations include various amounts of the following components: curcumin, genistein, squalamine, Vitamin E, N-Acetyl Cysteine, Selenium (Methylselenocysteine), Zinc Gluconate (Zinc), B Complex, Lentinan, Coenzyme Q10, Acetyl-L-Carnitine, alpha-lipoic acid (Lipoic Acid), Resveratrol, and Vitamin C. In addition to these compounds, the formulation may also contain arabinoxylan and peperine. Each of these components are discussed in detail below.

Curcumin

Curcumin (Turmeric) is derived from a spice that comes from the root *Curcuma longa*, member of the ginger family, Zingaberaceae. It is bright yellow, and has been used as a coloring agent in food in the United States. In India, it has been used for centuries as a spice, as a food preservative, and for its various medicinal properties. Curcumin is one of the most extensively investigated and well-defined chemopreventive phytochemicals.

A large number of studies have identified the antioxidant, anti-inflammatory, antiangiogenesis, antiviral, and antifungal properties of curcuminoids. A phase I human trial with 25 subjects using up to 8000 mg of curcumin per day for 3 months found no toxicity from curcumin. Five other human trials using 1125-2500 mg of curcumin per day have also found it to be safe. These human studies have found some evidence of anti-inflammatory activity of curcumin. These results have been confirmed in numerous studies. It exerts its anti-inflammatory activity by downregulating proinflammatory cytokines such as TNF, IL-1, IL-2, IL-6, IL-8 and IL-12 through possibly the inhibition of the transcription factor, NF-kappaB.

In phase I clinical studies, curcumin with doses up to 3600-8000 mg daily for 4 months did not result in discernable toxicities except mild nausea and diarrhea. The pharmacologically active concentration of curcumin could be achieved in colorectal tissue in patients taking curcumin orally and might also be achievable in tissues such as skin and oral mucosa, which are directly exposed to the drugs applied locally or topically. The effect of curcumin was studied in patients with rheumatoid arthritis, inflammatory eye diseases, inflammatory bowel disease, chronic pancreatitis, psoriasis, hyperlipidemia, and cancer.

The robust activity of curcumin in colorectal cancer has lead to five phase I clinical trials being completed showing the safety and tolerability of curcumin in colorectal cancer patients. To date clinical trials have not identified a maximum tolerated dose of curcumin in humans with clinical trials using doses up to 8000 mg per day. The success of these trials has lead to the development of phase II trials that are currently enrolling patients. Overwhelming in vitro evidence and completed clinical trials suggest that curcumin may prove to be useful for the chemoprevention of colon cancer in humans.

There is evidence curcumin is a potent immunomodulatory. One of the important factors implicated in chemoresistance and induced chemosensitivity is NFkB and curcumin has been shown to down regulate NFkB and inhibit IKB kinase thereby suppressing proliferation and inducing apoptosis. It possesses diverse anti-inflammatory and anti-cancer properties following oral or topical administration. Apart from curcumin's potent antioxidant capacity at neutral and acidic pH, its mechanisms of action include inhibition of several cell signaling pathways at multiple levels, effects on cellular enzymes such as cyclooxygenase and glutathione S-transferases, immuno-modulation and effects on angiogenesis and cell-cell adhesion. Curcumin's ability to affect gene transcription and to induce apoptosis in preclinical models is likely to be of particular relevance to cancer chemoprevention and chemotherapy in patients.

There are a number of metal chelates with curcumin that show cytotoxicity against cancer cells. Firstly, copper chelates of synthetic curcuminoids showed enhanced antitumor activity. All the compounds were found to be cytotoxic to cultured L929 cells, concentration needed for 50% inhibition being around 10 μg/ml for curcuminoids and 1 μg/ml for their copper complexes. Copper complex of cinnamyl curcumin which has an extended conjugation showed considerable activity in increasing the life span (ILS=78.6%) of ascites tumor-bearing animals. Copper chelates of curcuminoids showed a significant reduction ($p<0.001$) of solid tumor volume in mice. Curcumin possess anticancer and apoptosis-inducing properties in cancer cells. A mechanism has been proposed for the cytotoxic action of these compounds against cancer cells that involves mobilization of endogenous copper and the consequent prooxidant action. Furthermore, curcumin acted as a prooxidant causing copper-dependent DNA damage and the induction of apoptosis. Flow cytometry analysis showed that curcumin caused an apoptotic cell death of HL60 cells in a dose- and time-dependent manner. Curcumin can generate reactive oxygen species as a prooxidant in the presence of transition metals in cells, resulting in DNA injuries and apoptotic cell death. Secondly, a novel vanadyl curcumin complex (VO(cur)2) has been synthesized and its physicochemical properties characterized. VO(cur)2 was more effective as an anti-cancer agent, was more than twice as effective as curcumin alone as an anti-arthritic agent and was more than four times as effective as curcumin alone in inhibiting smooth muscle cell proliferation.

Curcumin has been shown to reduce the adenoma burden in rodent models of colorectal cancer. Patients with colorectal cancer ingested curcumin capsules (3,600, 1,800, or 450 mg daily) for 7 days. Biopsy samples of normal and malignant colorectal tissue, respectively, were obtained at diagnosis and at 6 to 7 hours after the last dose of curcumin. Blood was taken 1 hour after the last dose of curcumin. The results showed that a daily dose of 3.6 g curcumin achieves pharmacologically efficacious levels in the colorectum with negligible distribution of curcumin outside the gut.

Nasopharyngeal carcinoma (NPC) is a common malignant tumor in southern China. A complementary in vitro tumor model showed curcumin may induce apoptosis, and inhibit proliferation of CNE-2Z cells.

Curcumin could regulate the Raji and Ho-8910 cells and induce its apoptosis, so as to inhibit its proliferation, but with no significant cytotoxicity on human leukocytes.

There is significant experimental evidence suggesting that curcumin exerts multiple different suppressive effects on human breast carcinoma cells in vitro with MCF-7 cells. Curcumin inhibits the transcript levels of 2 major angiogenesis factors VEGF (vascular endothelial growth factor) and b-FGF (basic fibroblast growth factor) mainly in ER-negative MDA-MB-231 cells.

Interestingly, 9 angiogenesis-related genes were down-regulated over 5-fold in response to demethoxycurcumin, suggesting that the genetic reprogramming was crucially involved in anti-angiogenesis by this compound.

Epidemiological research on prostate cancer risk in men throughout the world has identified significant correlations between dietary habits and prostate cancer occurrence. One study recently reviewed preclinical and clinical data available for dietary agents such as curcumin and describes relevant clinical trials currently being conducted.

The published properties of curcumin include anti-cancer effects in animal model systems, metabolism, biological structure, pharmacokinetics, biological properties implicated in chemoprevention, antioxidant properties, influences upon phase I and II carcinogen-metabolizing enzymes, signal transduction properties and the neoplastic phenotype, apoptosis evasion, cell proliferation, de-differentiation, migration and invasion, and clinical studies. One study reviewed curcumin clinical research and summarized the unique properties of curcumin that may be exploited for successful clinical and cancer prevention.

Genistein

Genistein (4'5,7-trihydroxyisoflavone) occurs as a glycoside (genistin) in the plant family Leguminosae, which includes the soybean (*Glycine max*).

Many publications discuss genistein's antitumor capabilities and its mechanism of action in normal and malignant human and animal cells. Epidemiology suggests that genistein may reduce the risk of tumor formation. The mechanisms of action include the inhibition of protein tyrosine kinase (PTK), the inhibition of topoisomerase II, the down regulation of the expression of about 11 genes, including VEGF. Genistein can also inhibit the expression of gangliosides and other carbohydrate antigens that can mask immune recognition. Genistein works synergistically with tamoxifen, cisplatin, 1,3 bis 2-chloroethyl-1-nitrosurea, dexamethasone, daunorubicin and tiazofurin, and bioflavanoid food supplements such as quercetin, green-tea catechin, and black-tea arubigins. Genistein increases melanin production to protect melanocytes of the skin of Caucasians from UV-B radiation-induced melanoma.

Genistein is believed to have the potential to lower the incidence of metastatic prostate cancer. Genistein is shown to have kinase inhibitory effects in vivo. The specific suppression of focal adhesion kinase activity was shown to precede induction of apoptosis.

Genistein has been reported to be a natural chemopreventive in several types of human cancer, being shown to induce arrest of the cell cycle and apoptosis of bladder cells. Among isoflavones tested, genistein has proven to be the most potent inhibitor of angiogenesis in vitro and in vivo. Genistein has exhibited a dose-dependent inhibition of expression and excretion of vascular endothelial growth factor and platelet-derived growth factor.

A mixture of isoflavones produces a synergistic effect that causes even greater anti-tumorigenic effects than any single compound with the values of most cancer cell lines (3-5 μg/ml or 7.9 μM) within the reach of isoflavones. Genistein also shows to be preventative for human urinary tract infection. Genistein was shown to not exhibit toxicity to normal bladder cells with the normal physiological range of urine excretion (10 µg/ml). Anti-angiogenesis is one of the important mechanisms in explaining how soy isoflavones are anti-cancerous.

The resistance of renal cell carcinoma (RCC) to traditional therapies or systemic therapies, where only a small percentage of patients actually benefit from immunotherapy with INF and IL-2, leave few if any options that may be effective. Genistein has been identified as a viable treatment option. Genistein is a natural derivative of an isoflavone found in soybeans. Genistein is increasingly being found to treat other types of cancer by a multidimensional approach. At the cellular level, genistein inhibits cell proliferation, induces apoptosis, induces differentiation, and modulates cell cycle progression. At the molecular level, genistein inhibits the activity of protein tyrosine kinase, topoisomerase II, aromatase, and 17β-hydroxysteroid oxidoreductase.

Genistein is antiangiogenic in vitro and in vivo. Genistein has strong inhibitory effects on the expression of VEGF mRNA and bFGF in RCC cell lines in vitro. VEGF and bFGF are the main angiogenic factors in RCC, so genistein may be antiangiogenic in vitro, but the effect is unknown in vivo. Genistein has been shown to have an inhibitory effect on cell proliferation in leukemia, neuroblastoma, rhabdomyosarcoma, prostate cancer, and bladder cancer.

The National Cancer Institute is examining genistein as an oral chemotherapeutic for prostate cancer. Those on a Western diet typically have low levels of blood isoflavones. Mean plasma/serum genistein were 5.7 nmol/L in an American study, while the concentration in a Japanese study was 248 nmol/L (range, 90 to 1204 nmol/L). With soy supplementation excretion half-lives for genistein is seven hours.

Protein tyrosine kinases (PTKs) play an important role in cell growth. PTKs are associated with cell receptors for EGF, platelet-derived growth factor (PDGF), insulin and insulin-like growth factors (IGF), suggesting that tyrosine phosphorylation plays an important role in cell proliferation and transformation.

Topoisomerases introduce transient breaks in DNA. They participate in DNA replication, transcription, integration, and transposition and are also related to transformation by ras-oncogenes. Genistein inhibits the formation of a covalent complex between topoisomerase II and DNA and suppressed the growth the transformed cells.

Human cancer cell experiments show that genistein can induce apoptosis by: fragmentation of DNA; activation of caspase-3 (CPP32b); cleavage of poly (ADP-ribose) polymerase (PARP); downregulation of Bcl-2 (apoptosis inhibitor); enhancement of Bax protein (antagonizes the anti-apoptotic function of Bcl-2); increase of Bax:Bcl-2 ratio; induction of p21WAF1, which downregulates cyclin B and thereby arrest the cell cycle at the G2/M phase and promotes apoptosis by p53-independent pathway and causes inhibition of the activation of NKkB.

Genistein is considered to enhance the cytotoxicity of radiation. In Reuber H35 hepatoma cells, survival was reduced by a factor of 20 with irradiation alone and by a factor of 10000 when radiation was administered in the presence of genistein. Based on similar findings in prostate cancer, one study recommends a potential combination of genistein with radiation for the treatment of prostate cancer. The radiation enhancement is attributed to inhibition of topoisomerase II activity, which is involved in replication, transcription and probably DNA repair.

One study reported that a daily intake of 40 grams of soybeans may significantly lower serum levels of prostate-specific antigen (PSA). One study has reported that 44 days of treatment with genistein plus a polysaccharide from Basidiomycetes reduced serum PSA levels by 4.2 ng/mL from a pretreatment level, and genistein can decrease PSA mRNA. Serum PSA appears to be a useful measure of genistein's efficacy alone or in combination with irradiation or chemotherapeutic drugs for prostate cancer.

Although genistein has many potentially therapeutic actions against cancer, its biphasic bioactivity (inhibitory at high concentrations and activating at low concentrations) requires caution in determining therapeutic doses of genistein alone or in combination with chemotherapy, radiation therapy, and/or immunotherapy.

Genistein showed an up-regulation of angiogenesis inhibitors-plasminogen activated inhibitor-I, endostatin, angiostatin, and thrombospondin-1. Endostatin and angiostatin are novel molecular targets of genistein. Investigations shows more evidence that soy-based foods are natural dietary supplements promoting the inhibition of tumor angiogenesis. Endostatin has a direct anticancer action through blocking the activation of MMP-2, -9, and -13, in tumor cells. Angiostatin significantly inhibits the growth and MVD of human bladder cancer in SCID mice. Genistein upregulates endostatin and angiostatin to provide novel mechanisms for isoflavones to reverse the angiogenic switch of epithelial cancer. Isoflavones also suppress the growth and DNA synthesis of endothelial cells in vitro. Some of the biochemical targets of soy isoflavones that are over-expressed in endothelial tumor tissue include TF, VEGF, PDGF and MMP-2. Soy isoflavones are believed to have a combination of suppression effects on tumor cells.

Angiogenesis is presently one of the powerful strategies for treating cancer, and endothelial cells play a pivotal role in the process of angiogenesis. Several in vitro studies document the inhibition of angiogenesis by genistein. One has shown that genistein decreased vessel density and the production and release of vascular endothelial growth factor (VEGF) and TGF-β1. Another has shown that genistein downregulated 11 genes including VEGF. IN U87 and HT1080 renal carcinoma cells. Genistein, a tyrosine kinase inhibitor, is known to inhibit both tumor growth and angiogenesis. The precise molecular mechanism(s) by which genistein affects endothelial cells was investigated using cDNA microarrays. There were 256 genes of human umbilical vein endothelial cells (HUVECs) affected by 10 microM genistein that showed an altered expression of more than two fold. Among them were the genes related to cell proliferation, adhesion, transcription, translation, metabolism, cytoskeleton, apoptosis, kinases, and functionally unknown. Genistein affects endothelial cells as a negative mediator of proliferation and angiogenesis in vitro, partially by down-regulating cell adhesion-related genes and impairing cell adhesion. The incidence of hormone-related diseases such as prostatic, breast, ovarian, and endometrial cancer is lower in Asian populations compared to Western countries. Genistein is postulated to be responsible for the lower incidence of hormone-related disease. At physiological concentrations, genistein is able to elicit pleiotropic effects on a variety of pathways believed to be involved in tumorigenesis.

Genistein enhances antitumor activities of several chemotherapeutic agents. Genistein increases the antiproliferative effect of cisplatin 1.3 fold-in HTB-186 medulloblastoma cell line. In one study evaluating the in vitro and in vivo antileukemic activity of genistein, genistein produced a dose- and time-dependent antineoplastic activity against myeloid and lymphoid leukemic cell lines. Genistein treatment of the leukemic cells reactivated tumor suppressor genes that were silenced by aberrant DNA methylation. Due to the longer half-life of genistein in humans, a soy-enriched diet has the potential to produce plasma levels of this isoflavone in the range of concentration in vitro that produced an antileukemic activity. There is strong molecular in vivo evidence in support of our hypothesis that inactivation of the NF-kappaB signaling pathway by genistein results in the chemo-sensitization of pancreatic tumors to cisplatin.

Other in vitro studies have reported that the effect of genistein is enhanced by polyphenol food supplements including: curcumin, epigalloeicatechin, EGCG (green-tea derived) and thearubigin (black-tea derived), and by mineral such as vanadium. Genistein in combination with green-tea polyphenol EGCG induced apoptosis and enhanced p53 immunoreactivity in the 184-b5 breast cancer cell line.

The development of cancer is associated with disorders in the regulation of the cell cycle with known sequence of events that regulate cell cycle progression including protein kinase complexes composed of cyclin and cyclin-dependent kinase (CDK) molecules. The cyclins are CDK binding partners which are required for kinase activity and their protein levels are intimately link to the cell cycle stage. Dietary agents identified in fruits and vegetable can act to modulate the effects of deregulated cell cycle check points, such as curcumin, resveratrol, and genistein.

Cancer prevention strategies making use of combined agents with distinct molecular mechanisms, rather than individual agents, are considered promising for higher efficacy and lower toxicity. Genistein also appears to have prophylactic value; studies report a reduced risk of cancer among Japanese and Finnish populations that have a high consumption of genistein. Genistein as food supplement can be given to women from prepubertal stage of life so that it would be beneficial in arresting tumor initiation. Genistein may avoid the risk of developing cancer in both men and women who have risk factors for gender-based cancers, such as familial expression of BRCA 1 and 2. One study showed results that suggested genistein and synthetic structurally-modified derivatives of isoflavone may be promising agents for cancer chemoprevention and therapy either alone or in combination with existing chemotherapeutic agents.

Other studies has shown the difficulty in making definite statements or conclusions on clinical efficacy of genistein because of the great variability and differences of the study designs, small patient numbers, short treatment duration and lack of a standardized drug formulation. One study examined associations between nutritional and other lifestyle factors and the prevalence of prostate cancer in a case-control study of Japanese men. Two hundred patients and 200 age-matched controls (+/−5y) were selected from 3 geographic areas of Japan. Findings indicated that isoflavones might be an effective dietary protective factor against prostate cancer in Japanese men. Also, soy foods and enterolactone metabolized from dietary lignans protect against prostate cancer in older Scottish men. Furthermore, another study found that isoflavone intake was associated with a decreased risk of localized prostate cancer.

In summary, these reports indicate that genistein, a naturally occurring isoflavonoid, exhibits strong, direct anticancer and antiangiogenic activity. The biological effects of genistein are the inhibition of tyrosine kinases and the inhibition of hypoxic activation of hypoxia-inducible factor-1 (HIF-1), one of the main regulators in the inhibition of VEGF and other angiogenic gene expression.

Squalamine

Cartilage is a natural source of material with strong antiangiogenic activity. Clinical information on shark cartilage and drugs such as neovastat and squalamine has been demonstrated. Because their entire endoskeleton is composed of cartilage, sharks are thought to be an ideal source of angiogenic and tumor growth inhibitors. Shark cartilage extract has shown antiangiogenic and antitumor activities in animals and humans. The oral administration of cartilage extract was efficacious in reducing angiogenesis. Squalamine, a low molecular weight aminosterol, showed strong antitumor activity when combined with chemotherapeutic materials.

Squalamine is an anti-angiogenic molecule with a unique mechanism of action that blocks endothelial (blood vessel) cell activation, migration and proliferation by multiple growth factors. Squalamine's intracellular blockade of multiple growth factors contrasts with many other angiogenesis inhibition programs. The angiogenic tissue inhibitor of metalloprotease 3 (TIMP-3) and tumor suppressor protein (snm23) genes from shark cartilage were cloned and characterized.

Squalamine has demonstrated antiangiogenic properties in multiple clinical trials, both as a single-agent and in combination with standard chemotherapy. Squalamine blocks the action of a number of angiogenic growth factors, including vascular endothelial growth factor (VEGF). The mechanism of action is due to the specific entry of squalamine into activated endothelial cells through membrane invaginations known as caveolae. This unique mechanism has three principal anti-angiogenic effects on endothelial cells: 1) blockage of cell signals from multiple growth factors including VEGF and bFGF, altering cellular activation and cell division; 2) decreased expression of surface integrin alpha-v-beta-3, altering cell-cell interactions; and 3) altered cytoskeletal structure, decreasing motility. Squalamine has been granted Orphan Drug designation for the treatment of ovarian cancer by the U.S. Food and Drug Administration (FDA). Squalamine has been found in a therapeutic clinical trial to have positive results against non-small cell lung cancer (NSCLC).

A Phase I study of squalamine, a novel antiangiogenic agent originally isolated from the dogfish shark, *Squalus acanthias*, was conducted in patients with advanced cancers to: (a) determine the maximum tolerated dose (MTD), dose-limiting toxicity (DLT) and pharmacokineties of squalamine lactate when given as a 120-h continuous IV infusion every two weeks; and (b) to obtain information on prolonged (>120-h) continuous IV infusions in patients who have tolerated 120-h infusions. Preclinical evidence of synergy with cytotoxic agents and demonstration of human safety from this trial, have shown efficacy in, patients with late stage lung cancer and ovarian cancer.

The phase IIa trial in non-small cell lung cancer was designed to exam the preliminary efficacy and safety of Squalamine and combined with the standard chemotherapeutic agents carboplatin and paclitaxel. In patients with Stage IIB or Stage IV advanced disease. Objective responses (about 500 mg/day based on a 160 lb. male or 120 lb. female) were observed in 36% of patients receiving 300 mg/m$^2$/day for one or more cycles. Thirty-one percent of patients (11 of 36) experienced an objective response. An objective response was defined as 50% or greater reduction in tumor size.

A phase I/IIA study was designed to assess the safety, clinical response, and pharmacokinetics of squalamine when administered as a 5-day continuous infusion in conjunction with standard chemotherapy every 3 weeks in patients with stage IIIB (pleural effusion) or stage IV non-small cell lung cancer. The starting dose of squalamine was 100 mg/m$^2$/day and escalated to 400 mg/m$^2$/day; two of three patients at 400 mg/m$^2$/day had dose-limiting toxicity that included grade ¾ arthralgia, myalgia, and neutropenia. The combination of squalamine given continuously daily for 5 days, with paclitaxel and carboplatin given on day 1, is well tolerated.

At the recommended Phase II dose of 500 mg/m$^2$/day, squalamine is well tolerated and results in plasma concentrations at least an order of magnitude higher than those required for prominent antiangiogenic effects in preclinical studies. Preclinical studies have demonstrated that systemic squalamine administration in primates leads to inhibition of the development of ocular neovasculation and partial regression of new vessels. The dose for squalamine to produce these effects is 12 mg/m$^2$ twice weekly, which is less than 10% of the doses currently being used successfully in squalamine clinical trials for patients with advanced cancers.

Angiogenesis resulting from age-related macular degeneration (AMD) is the leading cause of legal blindness among adults age 50 or older in the Western world. About 25-30 million people are affected globally, with this number expected to triple over the next 25 years. Anti-vascular endothelial growth fact (VEGF)-A therapy has revolutionized the treatment. The drug binds to a "chaperones" calmodulin to a intracellular compartment and blocks angiogenesis at several levels. VEGF-A has been implicated in recent years as the major factor responsible for neovascular and exudative disease of the eye. AMD appears to come in two types: the "dry" form and the more severe "wet" form. Dry AMD, the more common and milder form of AMD, accounts for 85% to 90% of all cases. Dry AMD results in varying forms of sight loss and may or may not eventually develop into the wet form. Although the wet form of AMD accounts for only 10-15 percent of all AMD, the chance for severe sight loss is greater. It is responsible for 90 percent of severe vision loss associated with AMD. Approximately 500,000 cases of wet AMD are diagnosed annually worldwide. In North America alone, approximately 200,000 new cases of wet AMD are diagnosed each year. Wet AMD is caused by the growth of abnormal blood vessels, choroidal neovascularization (CNV), under the central part of the retina of the macula.

Squalamine shows strong anti-angiogenic activity in vitro. The primary actions include blockade of mitogen-induced actin polymerization, cell-cell adhesion and cell migration, leading to suppression of endothelial cell proliferation. Squalamine was found to exhibit little systemic toxicity and was generally well tolerated by treated patients with various solid tumor malignancies, including ovarian, non-small cell lung and breast cancers.

Xenograft tumor shrinkage was seen for the MV-522 tumor in combination treatments including squalamine, whereas no tumor shrinkage was seen when squalamine was omitted from the treatment regimen. Squalamine treatment was found to retard two cellular events necessary for angiogenesis, inducing disorganization of F-actin stress fibers and causing a concomitant reduction of detectable cell the surface molecular endothelial cadherin (VE-cadherin). The augmentation by squalamine of cytotoxicity from platinum-based therapies is attributable to interference by squalamine with the ability of stimuli to promote endothelial cell movement and cell-cell communication necessary for growth of new blood vessels in xenografts after chemotherapeutic injury to the tumor.

Several classes of agents now exist that target the different steps involved in angiogenesis. Drugs such as squalamine, celecoxib, ZD6126, TNP-470 and those targeting the integrins are also being evaluated in lung cancer. Squalamine is a natural antiangiogenic sterol, and its potential role in treatment of ovarian cancers with or without standard cisplatin chemotherapy was assessed. Since HER-2 gene overexpression is associated with cisplatin resistance in vitro and promotion of tumor angiogenesis in vivo, the response of ovarian cancer cells with or without HER-2 gene overexpression to squalamine and cisplatin was evaluated both in tumor xenograft models and in tissue culture. In in vitro studies, we found that squalamine does not directly affect proliferation of ovarian cells. However, squalamine significantly blocked VEGF-induced activation of MAP kinase and cell proliferation in human vascular endothelial cells (Li, et al., 2002).

The progressive growth and spread of many solid tumors depends, in part, on the formation of an adequate blood supply, and tumor angiogenesis has been reported to have prognostic significance in several human cancers. Therapy directed toward the vasculature of solid tumors is now being pursued as an important new direction in cancer treatment because avascular tumors exhibit only limited growth and tumor aggressiveness, and metastatic potential commonly correlates with tumor vascularity. Vascular endothelial growth factor (VEGF) is produced by most solid tumors and elicits a mitogenic effect on tumor-associated endothelial cells. VEGF binding to receptor tyrosine kinases triggers activation of downstream signaling enzymes, including MAP kinases which, in turn, regulate gene expression and specific endothelial cell responses including proliferation, migration and apoptosis. Several studies have suggested that VEGF plays an important role in the progression of many cancers. Growth factor pathways, such as those dependent on EGF and HER-2 receptors, appear to up-regulate VEGF production in solid tumors. Since EGF and HER family receptors are activated and/or overexpressed in significant numbers of human cancers, these growth factor receptor pathways may play a role in promoting further growth of human malignancy by increasing VEGF-dependent tumor angiogenesis.

The most potent antiangiogenic steroids are 11α-hydrocortisone and tetrahydrocortisol, which lacked mineralocorticoid or glucocorticoid activity and produced capillary regression in a chick embryo allantoic membrane assay. An endogenous metabolite of estrogen, 2-methoxyestradiol, has been found to inhibit proliferation, migration and invasion of endothelial cells in vitro as well as having antiangiogenic effects in certain in vivo tumor models. The mechanism of action of this compound is not yet fully elucidated, but its action does not seem to be mediated by classical steroid hormone receptors. Recent evidence has shown that 2-methoxyestradiol inhibits HIF-1α, a key angiogenic transcription factor, and is, thus, able to elicit a broad spectrum of cellular effects. This activity appeared to correlate with microtubule-depolymerizing properties of 2-methoxyestradiol. This steroidal compound is also reported to initiate apoptosis in both vascular endothelial and solid tumor cells. In preclinical models, 2-methoxyestradiol reduced tumor size and tumor-associated vascularization. In early clinical trials, this agent appears to be well tolerated by patients with cancer, and use of 2-methoxyestradiol is currently being evaluated in several different types of malignancy.

One mechanism of action of squalamine has been proposed to involve inhibition of the mammalian brush-border Na$^+$/H$^+$ exchanger isoform NHE3. The Na$^+$/H$^+$ exchanger is a transport protein that is known to regulate changes in cell volume or cell shape.

Squalamine was found to inhibit rat brain endothelial cell proliferation and migration induced by mitogens such as VEGF, bFGF, Platelet Derived Growth Factor (PDGF), and scatter factor/hepatocyte growth factor. In the absence of these mitogens, squalamine was found to have no direct effect on survival or proliferation of endothelial cells. In addition, squalamine was also found to inhibit proton secretion by mitogen-stimulated endothelial cells, a finding consistent with results reported by Akhter, et al. An interesting finding of this study involved the direct application of squalamine to a 4-day-old chick embryo vasculature. After only 20 minutes, squalamine elicited constriction of the smallest capillaries throughout the yolk sac, with entrapment of red cells. This acute remodeling process resulted in narrowed vascular segments and blocked erythrocyte movement and was confirmed by histological examination of treated and untreated yolk sacs. Since these new vessels are composed solely of endothelial cells, the luminal narrowing was concluded to be due to squalamine-induced changes in the shape or volume of endothelial cells. Immunohistochemical analyses of these tumors after treatment with squalamine revealed significant reductions in tumor-associated blood-vessel density.

In studies of human ovarian tumor-associated angiogenesis, ovarian cells were found to secrete significant levels of VEGF, a direct activator of angiogenesis, but squalamine did not reduce VEGF secretion by tumor cells, and it evoked no direct growth inhibition of ovarian cells in vitro. However, squalamine at doses as low as 160 nM did halt the proliferation of human vascular endothelial cells and markedly reduced VEGF-induced capillary tube-like formations by vascular endothelial cells growing in Matrigel culture. Squalamine interference with these downstream signaling pathways in vascular endothelial cells may be critical in disrupting the process of tumor-associated angiogenesis.

Studies have noted that squalamine as a single agent has a modest effect on tumor growth delay on rat 13762 mammary carcinoma, with squalamine dosing at 40 mg/kg. Moreover, it was found that the number of lung metastases decreased when mice were treated with squalamine. Specifically, by day 20, the numbers of metastases were reduced to half of those present in controls. Since lung metastases are actively implanting and growing using new blood vessels, this effect of squalamine suggests that it has strong antiangiogenic potency.

Previous studies have suggested that VEGF plays an important role in progression of ovarian cancer. Ovarian cancer is the most deadly gynecologic malignancy. Although advances in chemotherapy and surgery have helped to improve the overall survival of afflicted patients, 5-year survival rates from ovarian cancer remained about 44% in the early part of this decade. By the time many patients are diagnosed with ovarian cancer, peritoneal dissemination of the tumor has often occurred. This growth and spread of ovarian cancers depends, in part, on formation of an adequate blood supply. Tumor-associated angiogenesis is essential for growth of most solid tumors, and neovascularization has also been shown to have prognostic significance in epithelial ovarian cancer.

It is possible that treatment strategies directed to suppress the expression of VEGF and related angiogenic molecules may help to block tumor progression and reduce the morbidity associated with malignant ascites, Administration of squalamine in combination with cisplatin led to enhanced levels of apoptosis in several ovarian tumor cells assessed in vivo.

On the basis of strong evidence of antiangiogenic and antitumor properties of squalamine, it was selected for clinical development as a therapeutic agent for treatment of human malignancies. The investigators recruited 19 patients with an Eastern Cooperative Oncology Group (ECOG) performance status of $\leq 2$, with advanced non-leukemic cancers. Squalamine was administered as a continuous intravenous infusion over 120 h, with repeat dosing every 14 days. The best-tolerated dose of squalamine was found to be 192 mg/m$^2$/day, although a dose of 384 mg/m$^2$/day also appeared to be well-tolerated in patients without prior exposure to squalamine.

Natural products have served to provide a basis for many of the pharmaceutical agents in current use in cancer therapy and prevention. Squalamine, a natural steroidal compound, causes changes in vascular endothelial cell shape, and has been reported to possess significant antiangiogenic activity in models of lung, breast, brain and ovarian cancer. In addition, studies using Lewis lung carcinoma found that the number of metastasis were reduced by half after treatment, which confirms the antiangiogenic potency of squalamine. Squalamine exhibited little systemic toxicity in Phase I-II clinical trials and is well tolerated by treated cancer patients.

Since HER-2 gene overexpression is associated with cisplatin resistance in vitro and promotion of tumor angiogenesis in vivo, the response of ovarian cancer cells with or without HER-2 gene overexpression to squalamine and cisplatin was evaluated both in tumor xenograft models and in tissue culture. Profound growth inhibition was elicited by squalamine alone and by combined treatment with squalamine and cisplatin for both parental and HER-2-overexpressing ovarian tumor xenografts. Vascular endothelial growth factor (VEGF) is produced by most solid tumors and elicits a mitogenic effect on tumor-associated endothelial cells, and several studies suggest that VEGF plays an important role in progression of ovarian cancer.

Squalamine has shown to be useful for the treatment of important diseases such as cancers (lung, ovarian, brain, and others), age-related macular degeneration (AMD) and the control of body weight in men. Squalamine, a natural steroidal compound initially found in several tissues of the dogfish shark, *Squalus acanthias*, causes changes in vascular endothelial cell shape and has been reported to possess significant antiangiogenic activity in models of lung, breast, brain and ovarian cancer. In the shark, squalamine is found primarily in sites of bile synthesis such as liver and gallbladder, but the aminosterol compound also occurs in smaller amounts in the spleen, testes, stomach, gills and intestine. In the laboratory, squalamine was originally found to have bactericidal activity against gram-negative and gram-positive bacteria, as well as some fungicidal qualities. More importantly, squalamine at relatively low doses was later shown to selectively inhibit the formation of new blood vessels. However, unlike previously described steroids, squalamine has significant structural differences and does not interact with glucocorticoid or mineralocorticoid receptors. It is a 7,24-dihydroxylated 24-sulfated cholestane steroid conjugated to a spermidine at position C-3. Squalamine has been demonstrated to be an angiostatic steroid by virtue of its inhibition of growth of vascular endothelial cells in culture, activity in the chick embryo chorioallantoic membrane assay and a rabbit corneal micropocket assay, as well as growth inhibition of gliomas and lung cancers in vivo. Squalamine is somewhat unique among most current anti-angiogenic agents in development because it inhibits endothelial cell proliferation and migration induced by a wide variety of growth factors, including Basic Fibroblast Growth Factor (bFGF) and VEGF. This broad antiangiogenic activity of squalamine may result from its inhibition of surface sodium-proton exchangers (thus altering intracellular pH and thereby impeding intracellular signaling by several growth factors) and other downstream signaling pathways in endothelial cells. Nevertheless, there are different theories about the mechanism of action of squalamine that remain to be investigated.

Vitamin E

Vitamin E is a water-soluble vitamin that acts as an antioxidant in helping to eliminate free radicals that will damage and impair the immune system, thus helping prevent cancer, cardiovascular disease, diabetes, anemia, cataracts, age-related diseases (such as Alzheimer's), and macular degeneration. It is important in the treatment of many cancers including throat, esophagus, stomach, colon, cervix, breast and the prostate gland. Vitamin E has been shown to protect healthy cells from the ravages of chemotherapy. Research shows Vitamin E promotes healthy circulation, blood clotting, healing, reduces scarring, lowers blood pressure, maintains healthy nerves and muscles by strengthening capillary walls, and promotes healthy skin and hair. Vitamin E is also very effective in protecting skin from the damage it can get from ultraviolet rays from spending too much time in the sun.

N-Acetyl Cysteine (NAC)

Antioxidants have been heralded as cancer-preventive compounds, generally because of their ability to neutralize reactive oxygen species (ROS). ROS can cause damage to DNA, protein, and lipids, and overproduction can be toxic to the cell. A number of laboratories have reported that antioxidants can induce apoptosis in cells. Although thiol compounds such as NAC are probably most closely associated with radical quenching, one of their most important functions is to act as cellular redox buffers by regulating protein thiol/disulfide composition. It is known that many transcription factors are active only when their sulfhydryl groups are in the reduced state. Two of the best studied of these are AP-1 and NF-κB. Reduced cysteine groups are important for the activity of p53, as well, potentiating its participation in apoptosis. All caspases, in addition to many other enzymes, including several src-related phosphokinases, contain cysteines in their active sites and require a reduced environment for optimal activity.

Radiographic contrast media is third leading cause of hospital-acquired acute renal failure, accounting for approximately 11% of cases. The incidence of radio contrast nephropathy (RCN) reported in the literature has ranged from 1% to 45%. Diabetes mellitus and pre-existing chronic kidney disease (CKD) appear to be the most important predictors of RCN. RCN is associated with both short- and long-term morbidity and mortality. Estimates of in-hospital mortality rates are as high as 34% in patients who develop acute renal failure compared with 7% in those who do not. NAC has been used in trials to equate the prevention of RCN in patients with pre-existing CKD. NAC reduces the risk for RCN in patients with CKD.

To model VEGF-dependent tumor angiogenesis in vivo and test the essential components of NAC-dependent anti-angiogenic activity, one study used a VEGF-dependent angiogenesis assay in the differentiated chicken chorioallantoic membrane (CAM). When topical angiostatin was added, the overall vascular order was disrupted and microvessels appeared to abruptly terminate as evident in the gross transillumination images. Quantification of the angiogenic vascular counts alone, which do not account for defects in organization or function were evaluated independently. VEGF-expressing CAMs had a high-vascular density as expected. Treatments with either NAC or angiostatin significantly reduced the total vessel number to nearly half the level of the VEGF controls. On study suggests that NAC may show potential as an anti-tumorigenic agent with efficacy in preventing initial tumor take and metastasis along with a repression of VEGF expression in an experimental Kaposi's sarcoma model. NAC treatment did not repress the level of VEGF, which was still significant in hypoxic tumor microenvironments. The efficacy of NAC on the growth and viability of human breast carcinoma xenografts indicated that it is the tumor center that was predominantly affected by systemic NAC treatment, particularly with a dramatic loss of intratumoral vascular maintenance. NAC may not primarily affect the initial formation of new blood vessels, because the vascularity in the periphery of the tumors was unaffected by NAC. However, selective NAC antiangiogenic efficacy was shown in the "heart" of established tumors. An interesting result of the vascular depletion in the center of the tumor was that metastasis to draining lymph nodes was also affected. In addition it has been shown that NAC has direct effects on tumor cell.

Antioxidants such as NAC have been known to be cytoprotective after exposure to cellular damaging agents such as reactive oxygen species. NAC is a precursor to the cellular antioxidant glutathione (GSH), a scavenger for cell and DNA-damaging oxygen species such as hydrogen peroxide, superoxide, and lipid peroxides. In numerous studies, NAC has been shown to provide significant protection for stress-related cell and genomic damage. In addition, NAC has been found to be safe and efficacious in the clinic for treating acute respiratory distress and inflammation, as well as being a useful antidote for acute drug intoxication, e.g., Tylenol.

Sepsis remains the principal cause of mortality in patients on the intensive care unit despite improvements in supportive and antimicrobial therapies. The host response to infection or trauma is mediated by cytokines, arachidonic acid metabolites, reactive oxygen species, nitric oxide, and adhesion molecules. Although these mediators are essential for the resolution of infection and injury, prolonged production may result in host tissue and organ damage. Gene expression of these mediators is controlled in part at the transcription level via nuclear factor (NF)-[kappa]B. (NF)-[kappa]B is present in the cytoplasm, retained in an inactive form through interaction with its inhibitory subunit, I[kappa]B. Activation in response to lipopolysaccharide (LPS), cytokines, and other mediators occurs through a common pathway involving oxidative stress, resulting in phosphorylation of the I[kappa]B, allowing exposure of a nuclear recognition site and migration of the active (NF)-[kappa]B in to the nucleus, where it binds to target DNA. (NF)-[kappa]B has been shown to be involved in the up-regulation of many cytokines and chemokines, including interleukin-6 (IL-6) and IL-8, and adhesion molecules, including intercellular adhesion molecule (ICAM)-1. It has been shown in numerous studies, that (NF)-[kappa]B is activated in critically ill patients, particularly in those patients who do not survive. Inhibition of (NF)-[kappa]B release is likely to attenuate cytokine and adhesion molecule production and therefore may be beneficial. (NF)-[kappa]B activation and cytokine and adhesion molecule gene expression are decreased by NAC in vitro, and in various animal models of sepsis, NAC reduces adherence and chemotaxis, blunts cytokine responses, and improves survival. In critically ill patients, administration of NAC attenuates IL-8 release, increasing respiratory burst, decreases markers of free radical damage, improves oxygenation ratios, increases cardiac index and increases gastric intramucosal pH.

One study showed that administration of NAC in patients with severe sepsis is associated with attenuation of (NF)-[kappa]B activation in mononuclear leukocytes and decreased circulating concentrations of IL-8. No effect on IL-6 of sICAM-1 was observed. An oxidative step in the activation cascade of (NF)-[kappa]B is generally accepted, and several antioxidants have been shown to inhibit (NF)-[kappa]B activation in both in vitro and in animal models. Thiol antioxidants, typified by NAC, are known to induce p53-dependent apoptosis in transformed mouse embryo fibroblasts but not in normal mouse embryo fibroblasts, while suggested that NAC may show potential as an anti-tumorigenic agent with efficacy in preventing initial tumor take and metastasis along with a repression of VEGF expression in an experimental Kaposi's sarcoma model. The data presented here indicated that NAC treatment does repress the level of VEGF expression in experimental breast tumors. However, the moderate level of repression did not necessarily explain the significant loss in tumor viability. In addition, it was apparent that VEGF expression was still significant in hypoxic tumor microenvironments, thus defining focal areas of high VEGF expression.

The efficacy of NAC on the growth and viability of human breast carcinoma xenografts indicated that it is the tumor center that was predominantly affected by systemic NAC treatment, particularly with a dramatic loss of intratumoral vascular maintenance. Another study has suggested that NAC does not primarily affect the initial formation of new blood vessels, because the vascularity in the periphery of the tumors was unaffected by NAC, indicating selective NAC efficacy in the "heart" of established tumors. An interesting result of the vascular depletion in the center of the tumor was that metastasis to draining lymph nodes was also affected. In addition it has been shown that NAC has direct effects on tumor cell metastasis.

The effect of in vivo and in vitro NAC treatment on destructive activity of macrophages against patient's opportunistic infection with Candida received NAC (600 mg) or placebo orally 3 times a day for 15 days. NAC treatment significantly enhanced antifungal activity of peripheral blood monocytes (PBM) from these patients. Such study concluded that long-term NAC treatment could augment resistance against microbial infections which are often life-threatening in these patients.

In conclusion, NAC, taken daily for a long-term period, has very low toxicity and results in the improvement of biological markers which are predictive for patient outcome Furthermore, NAC has shown its potential role in the functional restoration of the immune system in advanced cancer patients.

Selenium (Methylselenocysteine)

Selenium (Se) is an essential element which is involved in various biological processes in nearly all tissues of animals and human, e.g. protection against oxidative stress in the cardiovascular system, and may play a role in cancer protection. Selenoprotein P (SeP) is a highly glycosylated plasma protein containing up to 10 selenocysteine residues. It is secreted by hepatocytes and also by the human hepatoma cell line HepG2.

The precise mechanisms of apoptosis induced by various selenium compounds are not well understood. Sodium selenite induced apoptosis is accompanied by increased Bax expression. One study showed association between antioxidant use and primary cancer incidence and mortality and evaluated these effects across specific antioxidant compounds. Selenium supplementation might have anticarcinogenic effects in men and thus requires further research. Doxorubicin and selenium cooperatively activate Fas signaling leading to apoptosis. The use of antioxidants during chemotherapy has been shown to reduce or prevent the undesirable effects experienced by healthy cells. Micronutrient selenium is well known for its antioxidant properties. Selenomethionine is effective in reducing the genetic damage induced by the antitumoral agent doxorubicin.

Prostate cancer is the most commonly diagnosed malignancy in males. One study showed the natural products with the greatest potential to reduce the risk of prostate cancer, including lycopene, vitamin E, selenium, vitamin D, soy and green tea. Although recent reports suggest that selenium can modulate the activity of cytotoxic drugs, the mechanism underlying this activity remains unclear. This has been investigated using a panel of human B-cell lymphoma cell lines. Taken together, these results show that the NF-kappaB pathway is one target for methylselenic acid (MSA) underlying the interaction between MSA and chemotherapy.

Selenium is incorporated in the proteome in the form of the genetically encoded amino acid selenocysteine, which is the characteristic component of the selenoproteins. One researcher investigated the expression of the selenoenzyme GPx-2 which is predominantly present in the tissues of the gastrointestinal tract such as the small intestine and therefore named gastrointestinal glutathione peroxidase. The GPx-2 activity in the Se-deficient rat colon samples was 6.8 fold lower than in the Se-adequate rats in contrast to 1.2 fold lower levels between the corresponding samples in the small intestine. This finding might explain the different susceptibility of the colon and the small intestine to cancer and support the theory of the protective effect of selenium in the gastrointestinal tract.

Damage to DNA and other cellular molecules by reactive oxygen species ranks high as a major culprit in the onset and development of colorectal cancer. Expression of 14 oxidative stress-related molecules in both tumorous and non-tumorous tissues in 41 patients was examined by immunohistochemistry and Western blot analysis. These data suggest that contrasting expression pattern of the antioxidant selenoproteins plays an important role in the progression of colorectal cancer. Most known chemopreventive agents including certain selenium compounds suppress the activation of the nuclear factor kappaB (NF-kappaB).

Selenium methylselenocysteine (Se-MeSeCys) is a common selenocompound in the diet with a tested chemopreventive effect. One study showed that treatment of HepG2 cells with concentrations of Se-MeSeCys in the nanomolar to micromolar range confers a significant protection against an oxidative insult.

The thyroid gland has an exceptionally high selenium content, even during selenium deficiency. At least 11 selenoproteins are expressed, which may be involved in the protection of the gland against the high amounts of H2O2 produced during thyroid hormone biosynthesis.

Zinc (Zinc Gluconate)

Zinc is an essential trace element for human health and is a critical component of over 300 enzymes and transcription factors involved in DNA damage response and repair. The prostate is known to accumulate high levels of zinc, but levels are markedly decreased with cancer development. Zinc deficiency may compromise DNA integrity in the prostate by impairing the function of zinc-containing proteins B-Complex Vitamin B1 or Thiamine, as it is more commonly referred to now, is one of the most important members of the B group of vitamins. Thiamine promotes growth, protects the heart muscle, and stimulates brain action. It plays an important role in the normal functioning of the entire nervous system. It aids digestion, especially of carbohydrates. It has a mild diuretic effect: that is it increases urine formation. It improves peristalsis and helps to prevent constipation. It also helps to maintain the normal red blood count, improves circulation, and promotes a healthy skin. It protects against the damaging effect of lead poisoning, and prevents oedema or fluid retention in connection with heart ailments. It also reduces fatigue, increases stamina, and prevents premature ageing and senility by increasing mental alertness. Like other vitamins of the B complex group, it is more potent when combined with other B vitamins rather than used separately.

Vitamin B2 or Riboflavin is the second member of the B complex group. Riboflavin is essential for growth and general health. It functions as a part of a group of enzymes which are involved in the metabolism of carbohydrates, fats and proteins. It is involved in a number of chemical reactions in the body and is therefore essential for normal tissue maintenance. Riboflavin aids digestion and helps in the functioning of the nervous system. It prevents constipation, promotes a healthy skin, nails and hair, and strengthens the mucous lining of the mouth, lips and tongue. Riboflavin also plays an important role in the health of the eyes and alleviates eye strain. This vitamin is particularly helpful in counteracting the tendency towards glaucoma. An ample supply of vitamin B2 provides vigour and helps to preserve the appearance and feeling of youth.

Vitamin B3 or Niacin is an important vitamin of the B group. Niacin in important for proper blood circulation and the healthy functioning of the nervous system. It maintains the normal functions of the gastro-intestinal tract and is essential for the proper metabolism of proteins and carbohydrates. It helps to maintain a healthy skin. Niacin dilates the blood vessels and increases the flow of blood to the peripheral capillary system. This vitamin is also essential for the synthesis of sex hormones, namely estrogen, progesterone, and testosterone, as well as cortisone, thyroxin, and insulin.

Vitamin B5 or Pantothenic Acid is a water soluble vitamin of the B complex group. Pantothenic Acid is a part of the enzyme system which plays a vital role in the metabolism of carbohydrates, fats and proteins, and in the synthesis of amino acids and fatty acids. It is also essential for the formation of porphyrin, the pigment portion of the haemoglobin molecule of the red blood cells. This vitamin is involved in all the vital functions of the body. It stimulates the adrenal glands and increases production of cortisone and other adrenal hormones. It is primarily used as an anti-stress factor and protects against most physical and mental stresses and toxins. Pantothenic Acid increases vitality, wards off infections, and speeds recovery from ill health. It helps in maintaining the normal growth and development of the central nervous system. This vitamin prevents premature ageing. It also provides protection against any damage caused by excessive radiation.

Vitamin B6 or Pyridoxine is a versatile vitamin of the B complex group. Pyridoxine aids in food assimilation and protein and fat metabolism, especially in the metabolism of essential fatty acids. It activates many enzymes and enzyme systems. It is involved in the production of antibodies which protect against bacterial diseases. Pyridoxine helps in the healthy functioning of the nervous system and brain. It is essential for the normal reproductive process and healthy pregnancies. This vitamin prevents nervous and skin disorders, provides protection against a high cholesterol level, certain types of heart disease, and diabetes. It prevents tooth decay.

Vitamin B6 regulates the balance between sodium and potassium in the body, which is vitally important for the normal body functions. It is also required for absorption of vitamin B12 and for the production of hydrochloric acid and magnesium. Vitamin B6 is now considered as a wonder treatment for a wide range of common ailments, such as, diabetes, hemorrhoids, convulsions in infants and women, vaginal bleeding, stress and insomnia, morning sickness and travel sickness.

Vitamin B8 or Biotin, is a member of the vitamin B complex group.

Vitamin B9 or Folic Acid, also known as folacin or folate, is another important member of the B complex group. Folic Acid in combination with vitamin B12, is essential for the formation, maturation and multiplication of red blood cells. It is necessary for the growth and division of all body cells, including nerve cells, and for manufacturing a number of nerve transmitters. It also produces nucleic acids, RNA(ribonucleic Acid) and DNA(Deoxyribonucleic Acid), that carry hereditary patterns. It aids in protein metabolism and contributes to normal growth. Folic acid helps in the building of antibodies which prevent and heal infections. It is essential for the health of the skin and hair, and helps to prevent premature graying of the hair. Folic acid is the significant important nutrient for a pregnant woman and her developing foetus. In fact, eating fresh fruits and vegetables rich in folate, from conception until the due date, is the best policy a woman can adopt to ensure that her pregnancy will be a happy and a healthy one. Folic acid also improves lactation. Large doses of folic acid has been found beneficial in the treatment of a few diseases which are rare such as, megaloblastic anaemia, sprue, recurrent abortion, mental retardation, brown spots on the skin and gout.

Vitamin B12 or Cyanocobalamin, another member of the B complex group is produced only by fungi and bacteria. Human intestinal bacteria also produced appreciable quantities of it. It was effective in a type of anaemia called pernicious anaemia, in as small a quantity as one-millionth part of a gram. Its deficiency in the body occurred usually due to malabsorption from the intestine rather than from malnutrition. This vitamin in destroyed by factors like sunlight, alcohol, estrogen, and sleeping pills. The presence of sufficient quantities of gastric juice is essential to facilitate its absorption in the intestine. Calcium and protein-rich food greatly help the absorption of this vitamin from the intestines. The amount of vitamin B12 which is not immediately needed by the body is stored in the liver, which is capable of storing relatively large amounts of this nutrient. About 30 mcg of vitamin B12 are excreted in the normal urine daily. When injected in a large dose up to 100 mcg, up to 90% of the quantity is excreted. This vitamin is also secreted in breast milk for the use of babies.

Like vitamin B6, vitamin B12 is essential for the production and regeneration of red blood cells. It is also needed for the proper functioning of the central nervous system. It improves concentration, memory, and balance and relieves irritability. Vitamin B12 is necessary for the proper utilisation of fats, carbohydrates and proteins for body building. It promotes growth and increases appetite in children. This vitamin is also involved in many vital metabolic and enzymatic processes, including the metabolism of folic acid. If the immune cells made in the bone marrow are to mature into active disease-fighters, a sufficient quantity of vitamin B12 and folic acid are necessary.

Lentinan

Numerous bioactive polysaccharides or polysaccharide-protein complexes from medicinal mushrooms are described that appear to enhance innate and cell-mediated immune responses, and exhibit antitumor activities in animals and humans. Of significant relevance and importance is the ability of particular mushroom-derived compounds to modulate the human immune response and to inhibit certain tumor growths. Those compounds which appear to stimulate the human immune response are being sought for the treatment of cancer.

One of the most significant factors of many of the derived bioactive polymers from medicinal mushrooms is their role as immune modulators. The body's defense against viral attack and against spontaneously arising malignant tumor cells comprises a dynamic orchestrated interplay of innate and acquired immune responses. Innate immunity, where macrophages, neutrophils, natural killer cells (NKC) and dendritic cells are gatekeepers, is regulated by chemical-messengers or cytokines and by activation of inflammatory and acute phase responses. Therefore, a fully functional immune response is critical to the recognition and elimination of tumor cells. The identification of mushroom derived compound(s) that are capable of stimulating components of innate or acquired immunities may be of potential benefit for cancer treatment.

Tumors may develop when transformed cells escape immunological host defense mechanisms. Indeed, spontaneous tumors in immunosuppressed individuals indicate that the immune system can provide a significant mechanism for host resistance against cancer and infectious diseases.

Lentinan is derived from a water extract of *Lentinus edodes mycelium* before the mushroom fruiting bodies develop and is protein-free being completely devoid of any nitrogen, phosphorous, or sulphur. Lentinan has proved successful in prolonging the overall survival of cancer patients, especially those with gastric and colorectal carcinoma. In a randomized controlled study of patients treated with tegafur or a combination of Lentinan and tegafur overall survival was significantly prolonged in the Lentinan plus tegafur group. Of 145 patients, 68 received tegafur alone, and 77 received Lentinan plus tegafur. The respective 50% survival times for the two groups were 92 days (tegafur alone) and 173 days (Lentinan plus tegafur).

Lentinan does not attack cancer cells directly, but produces its antitumor effect by activating different immune responses in the host. Lentinan has displayed various kinds of immune activities in both animals and humans (Table 1). Until recently, the interactions of Lentinan with many kinds of immune cells were not known. Research into receptor-binding in immune cells by β-glucans from fungi showed that β-glucans from yeast bind to iC3b-receptors (CR3, CD11b/CD18) of phagocytic cells and NKC, stimulating phagocytosis and cytotoxic degranulation, respectively. Lentinan can activate NKC in vitro in the same concentrations that are achieved in the blood plasma of patients treated clinically with Lentinan. Increased NKC activity is involved in tumor suppression and while these cells do not stimulate certain T-killer cell activity, or do so only under certain conditions, they are strong T-helper cell stimulants both in vitro and in vivo. Lentinan can inhibit prostaglandin synthesis, which can slow T-cell differentiation in animals and humans, as well as inhibiting suppressor T-cell activity in vivo.

Lentinan's immune-activating ability may be linked with its modulation of hormonal factors, which are known to play a role in tumor growth. The anti-tumor activity of Lentinan is strongly reduced by administration of thyroxine or hydrocortisone. Lentinan can also restore a tumor-specific antigen-directed delayed-type hypersensitivity (DTH) response. Interestingly, accumulating evidence suggests that Lentinan-stimulation of dendritic cells, which include antigen-presenting cells that are found in the lymph nodes, spleen and thymus; follicular and interdigitating dendritic cells; skin and other tissue Langerhans cells. Lentinan has an important impact on immunomodulation and anti-tumor activity. Moreover, dendritic cell tumor-infiltration in association with killer cytotoxic T cell stimulation and activation have been shown to have a governing role in tumor attack and elimination.

In summary, lentinan has been shown above in a significant number of studies to exert its anti-tumor activity by stimulating the innate and acquired immunity in their fight against virally infected cells and cancer cells.

Coenzyme Q10

Coenzyme Q10 (CoQ10, ubiquinone) is a compound whose actions resemble those of vitamin E. It is stored in the fatty tissues of the body, reducing the need to ingest large quantities. It stimulates the immune system, aids circulation, increases tissue oxygenation, and has anti-aging effects. It has the ability to counter histamine, and therefore is beneficial for people with allergies, asthma, or respiratory disease. It has been used to treat schizophrenia and Alzheimer's disease and is also beneficial in fighting obesity, multiple sclerosis, and diabetes. More than 12 million people in Japan are reportedly taking it at the direction of their physicians for treatment of heart disease. The amount of CoQ10 present in the body declines with age, so it should be supplemented in the diet, especially for those over the age of fifty.

Antioxidants are emerging as prophylactic and therapeutic agents. These are the agents which scavenge free radicals otherwise reactive oxygen species and prevent the damage caused by them. Free radicals have been associated with pathogenesis of various disorders like cancer, diabetes, cardiovascular diseases, autoimmune diseases, neurodegenerative disorders and are implicated in aging. Several antioxidants like SOD, CAT, epigallocatechin-3-O-gallate, lycopene, ellagic acid, coenzyme Q10, indole-3-carbinol, genistein, quercetin, vitamin C and vitamin E have been found to be pharmacologically active as prophylactic and therapeutic agents for above mentioned diseases. Results from several studies are positive. One study recommends a combination in which physiological amounts of vitamins C, D, K and B-complex, N-acetylcysteine, vitamin E of natural origin might be complemented by allopurinol, co-enzyme Q-10 and alpha-lipoic acid.

CoQ10's role as an antioxidant may be more powerful than Vitamin E. Antioxidants help the body deal with unstable chemicals called free radicals. Free radicals are produced by the body when food is converted into energy and will build up in the body over time. They increase the potential for damage to the body cells (a process called oxidative stress) which is associated with the aging process and a general decline in the central nervous system and the immune system. They are also thought to contribute to the development of various health conditions such as cancer, heart disease, and inflammation conditions for example arthritis. Furthermore antioxidants can help to prevent the conversion of nitrates found in tobacco smoke, bacon, and some vegetables into cancer-causing substances.

CoQ10 is an essential cofactor in the electron transport chain, serves as a potent antioxidant in mitochondria and lipid membranes, and is often used as a dietary supplement for a number of diseases including cardiovascular diseases. The identified CoQ10-inducible genes and pathways play an important role in inflammatory response. Due to the notable absence of clinically significant side effects and likely therapeutic benefit, CoQ10 can be considered a safe adjunct to standard therapies in cardiovascular disease. Preoperative oral coenzyme Q(10) therapy in patients undergoing cardiac surgery increases myocardial and cardiac mitochondrial coenzyme Q(10) levels, improves mitochondrial efficiency, and increases myocardial tolerance to in vitro hypoxia-reoxygenation stress.

One study showed that acute exercise increased free radical formation in human skeletal muscle. These findings provide the first direct evidence for intramuscular free radical accumulation and lipid peroxidation following acute exercise in humans.

Statins inhibit the production of CoQ10, which is required for mitochondrial electron transport. In one study, fifty consecutive new cardiology clinic patients who were on statin drug therapy (for an average of 28 months) on their initial visit were evaluated for possible adverse statin effects (myalgia, fatigue, dyspnea, memory loss, and peripheral neuropathy). All patients discontinued statin therapy due to side effects and began supplemental CoQ10 at an average of 240 mg/day upon initial visit. Patients have been followed for an average of 22 months with 84% of the patients followed now for more than 12 months. The prevalence of patient symptoms on initial visit and on most recent follow-up demonstrated a decrease in fatigue from 84% to 16%, myalgia from 64% to 6%, dyspnea from 58% to 12%, memory loss from 8% to 4% and peripheral neuropathy from 10% to 2%. The researchers concluded that statin-related side effects, including statin cardiomyopathy, are far more common than previously published and are reversible with the combination of statin discontinuation and supplemental CoQ10, and they saw no adverse consequences from statin discontinuation. Statin drugs (3-hydroxy-3-methylglutaryl coenzyme A reductase inhibitors) reduce the level of cholesterol by inhibiting the synthesis of mevalonate, an intermediary in the cholesterol biosynthetic pathway. Use of statin drugs has been associated with a variety of skeletal muscle-related complaints CoQ10, a component of the mitochondrial respiratory chain, is also synthesized from mevalonate, and decreased muscle CoQ10 concentration may have a role in the pathogenesis of statin drug-related myopathy. Statins decrease LDL cholesterol and the risk of atherosclerotic cardiovascular disease (CVD). They also decrease CoQ10, an effect that may negate some of the statin benefit on CVD.

An essential role of CoQ10 is as an electron carrier in the mitochondrial respiratory chain. Moreover, CoQ10 is one of the most important lipophilic antioxidants, preventing the generation of free radicals as well as oxidative modifications of proteins, lipids, and DNA, it and can also regenerate the other powerful lipophilic antioxidant, alpha-tocopherol. Decreased levels of CoQ10 in humans are observed in many pathologies (e.g. cardiac disorders, neurodegenerative diseases, AIDS, cancer) associated with intensive generation of free radicals and their action on cells and tissues. In these cases, treatment involves pharmaceutical supplementation or increased consumption of CoQ10 with meals.

Lowering of low-density lipoprotein cholesterol is well achieved by CoQ10. Statins inhibit the production of CoQ10 play an important role in statin-induced hepatopathy. CoQ10 supplementation protects cells from this complication and should be taken if statins are prescribed.

Neuronal cell death induced by oxidative stress is correlated with numerous neurodegenerative diseases, including Alzheimer's disease (AD), Parkinson's disease (PD), and stroke. Paraquat, a nonselective herbicide, was once widely used in North America and is still routinely used in Taiwan. Results indicate that water-soluble CoQ10 can prevent oxidative stress and neuronal damage induced by paraquat and therefore, can be used for the prevention and therapy of neurodegenerative diseases caused by environmental toxins. Furthermore, the manual workers of the gas-and-oil extraction industry (Russian Siberian extraction plants) are exposed to hostile environmental and occupational conditions, resulting in elevated mortality and disability, due to chronic neurological and cardiovascular diseases. The short term administration of a nutraceutical formulation based on CoQ10, vitamin E, selenium, methionine and phospholipids led to significant improvement of cardiovascular parameters and psycho-emotional status, consistent with the normalization of LDCL and peroxynitrite production by WBC, with a good compliance to treatment confirmed by the increased blood levels of ubiquinol. Finally, UV-C radiation is able to impair cellular functions by directly damaging DNA, and by inducing an increased formation of reactive oxygen species that leads to a condition of oxidative stress. Intracellular levels of ROS, mitochondrial depolarization and cell viability was measured by flow cytometry. Enhancing CoQ10 synthesis and suppressing the induction of NF-kappa B, may provide neuroprotection.

Brain aging and neurodegenerative disorders involve impaired energy metabolism and oxidative damage, but the involvement of the Plasma Membrane Redox System (PMRS) in these processes is unknown. Caloric restriction protects the brain against aging and disease by increasing the activities of PMRS. These findings suggest important roles for the PMRS in protecting brain cells against age-related increases in oxidative and metabolic stress. Enhancing CoQ10 synthesis and suppressing the induction of NF-kappa B, may provide neuroprotection.

The feasibility of using a coupled in vitro digestion-Caco-2 cell uptake as a model for examining the digestive stability and absorption of CoQ10 from a variety of commercially available CoQ10 products was examined. The CoQ10 uptake by the cells was correlated with the extent of micellarization of CoQ10 during simulated digestion. Most of CoQ10 taken up by the cells was converted to ubiquinol either during or following uptake.

CoQ10 is used by the body as an endogenous antioxidant. This property combined with its essential function in mitochondrial energy production suggests that it may have therapeutic potential in cancer treatment. As part of the body's antioxidant defense against free radical production, CoQ10 concentrations may change during anti-cancer chemotherapy. CoQ10 was measured in the plasma of 27 children with acute lymphoblastic leukemia (ALL) at the time of diagnosis, during induction (protocol ALL-BFM 2000), and post induction treatment. The starting values were compared to the CoQ10 concentrations in 92 healthy children. The total CoQ10 concentration and its redox status were measured by HPLC using electrochemical detection and internal standardization. While the CoQ10 concentration in the plasma of children with ALL was within a normal range at the time of diagnosis (0.99+/−0.41 pmol/ml), a drastic increase was observed during induction treatment (2.19+/−1.01 pmol/ml on day 33). This increase was accompanied by shift in the redox status in favor of the reduced form of CoQ10. The increase in CoQ10 concentration during induction treatment may be attributed to the activation of a natural antioxidative defense mechanism.

Anthracyclines are among the most effective chemotherapeutic agents in the treatment of numerous malignancies. Unfortunately, their use is limited by a dose-dependent cardiotoxicity. Preclinical and clinical studies suggest that anthracycline-induced cardiotoxicity can be prevented by administering CoQ10 during cancer chemotherapy that includes drugs such as doxorubicin and daunorubicin. Studies further suggest that CoQ10 does not interfere with the antineoplastic action of anthracyclines and might even enhance their anticancer effects. CoQ10, an essential component of the electron transport system and a potent intracellular antioxidant, appears to prevent damage to the mitochondria of the heart, thus preventing the development of anthracycline-induced cardiomyopathy.

Anthracycline-induced cardiotoxicity after treatment for childhood cancer is a serious problem. Dexrazoxane prevents or reduces cardiac injury without compromising the antileukemic efficacy of doxorubicin, and CoQ10 showed a strong protective effect on cardiac function during anthracycline therapy.

The prognostic significance of supplementing CoQ10, riboflavin and niacin (CoRN) along with tamoxifen to breast cancer patients was evaluated by measuring the serum cytokine levels of interleukin (IL)-1beta, IL-6, IL-8, tumor necrosis factor alpha (TNF-alpha) and vascular endothelial growth factor. In this study, 84 breast cancer patients were randomized to receive a daily supplement of CoQ(10) 100 mg, riboflavin 10 mg and niacin 50 mg, and a dosage of tamoxifen 10 mg twice a day. Serum cytokine levels were elevated in untreated breast cancer patients (Group II) and significantly reduced after tamoxifen therapy for more than 1 year (Group III). CoRN supplementation in breast cancer patients suggested a good prognosis and efficacy of the treatment, and might even offer protection from metastases and recurrence of cancer.

Tamoxifen (TAM), a non-steroidal anti-estrogen that is widely used in adjuvant therapy for all stages of breast carcinomas and in chemoprevention of high-risk group. The hepatic estrogenic effect of TAM induces hypertriglyceridemia by reduced activity of lipolytic enzymes (LPL) on triglycerides. CoQ10, riboflavin and niacin are proved to be potent antioxidant and protective agents against many diseases including cancer and cardiovascular diseases (CVD). The study figures the altered lipid and lipoprotein levels in the untreated and TAM-treated breast cancer patients. On combination therapy with CoQ10, riboflavin and niacin, it counteracts the tamoxifen-induced hyperlipidemia to normal levels.

The influence of menopause and hormone replacement therapy (HRT) on serum levels of CoQ10 and other lipid-soluble antioxidants in normal women have been studied. Serum levels of CoQ10, alpha-tocopherol, gamma-tocopherol, beta-carotene and lycopene were determined in 50 premenopausal women (not using oral contraceptives), 33 healthy postmenopausal and 15 postmenopausal women on HRT. The decrease in serum concentrations of CoQ10 produced by HRT, promotes oxygen free radical-induced membrane damage and may result in cardiovascular risk in postmenopausal women using HRT.

Early surgical intervention remains the most successful therapy for melanoma. Despite better outcomes observed in soft tissue and lymph node metastases, the results of pharmacological therapies are still disappointing. One study involved patients with stage I and II melanoma and surgically removed lesions. Treatment efficacy was evaluated as incidence of recurrences at 5 years. Long-term administration of an optimized dose of recombinant interferon alpha-2b in combination with CoQ10 seemed to induce significantly decreased rates of recurrence and had negligible adverse effects. Abnormally low plasma levels of CoQ10 have been found in patients with cancer of the breast, lung, or pancreas. Analysis of baseline plasma CoQ10 levels are a powerful and independent prognostic factor that can be used to estimate the risk for melanoma progression.

Free radicals have been implicated in the action of many chemotherapeutic drugs. Camptothecin and other chemotherapeutic drugs, such as etoposide, doxorubicin, and methotrexate, induce an increase in CoQ10 levels as part of the antioxidant defense against free radical production under these anticancer treatments in cancer cell lines. Chemotherapy treatment induced both free radical production and an increase in CoQ10 levels in all the cancer cell lines tested. Reduced CoQ10 form levels were particularly enhanced. Findings suggest that CoQ10 increase is implicated in the cellular defense under chemotherapy treatment and may contribute to cell survival.

Suggestions that CoQ10 might reduce the toxicity of cancer treatments have not been tested by rigorous trials. Further investigations are necessary to determine whether CoQ10 can improve the tolerability of cancer treatments.

In summary, CoQ10 plays a critical role in the production of energy in every cell of the body. It aids circulation, stimulates the immune system, increases tissue oxygenation, and has anti-aging effects. CoQ10 is an essential cofactor in the electron transport chain, serves as a potent antioxidant in mitochondria and lipid membranes. Statins inhibit the production of CoQ10 and thus play an important role in statin-induced hepatopathy. CoQ10 supplementation protects cells from this complication. Finally, CoQ10 is used as a dietary supplement for a number of diseases including cardiovascular diseases and cancer.

Acetyl-L-Carnitine

Peripheral neurotoxicity is a major complication associated with the use of chemotherapeutic agents such as platinum compounds, taxanes and vinca alkaloids. The neurotoxicity of chemotherapy depends not only on the anticancer agent(s) used, the cumulative dose and the delivery method, but also on the capacity of the nerve to cope with the nerve-damaging process. The sensory and motor symptoms and signs of neurotoxicity are disabling, and have a significant impact on the quality of life of cancer patients. Moreover, the risk of cumulative toxicity may limit the use of highly effective chemotherapeutic agents. Therefore, prophylaxis and treatment of peripheral neurotoxicity secondary to chemotherapy are major clinical issues. Acetyl-L-carnitine (ALC) plays an essential role in intermediary metabolism. Some of the properties exhibited by ALC include neuroprotective and neurotrophic actions, antioxidant activity, positive actions on mitochondrial metabolism, and stabilization of intracellular membranes. ALC has demonstrated efficacy and high tolerability in the treatment of neuropathies of various aetiologies, including chemotherapy-induced peripheral neuropathy (CIPN). In several experimental settings, the prophylactic administration of ALC prevented the occurrence of peripheral neurotoxicity commonly induced by chemotherapeutic agents. In animal models of CIPN, ALC administration promoted the recovery of nerve conduction velocity, restored the mechanical nociceptive threshold, and induced analgesia by up-regulating the expression of type-2 metabotropic glutamate receptors in dorsal root ganglia. These results, plus the favorable safety profile of ALC in neuropathies of other aetiologies, have led to the effects of ALC on CIPN being investigated in cancer patients. Preliminary results have confirmed the reasonably good tolerability profile and the efficacy of ALC on CIPN. ALC has several mechanisms, which include the regeneration of injured nerve fibers, reducing oxidative stress, supporting DNA synthesis in mitochondria and enhancing nerve growth factor concentrations in neurons.

Current studies support the use of ALC in cancer patients with persisting neurotoxicity induced by paclitaxel or cisplatin treatment.

ALC also enhances neurotrophic support of sensory neurons, potentially causing symptom relief and nerve regeneration, and in addition has numerous other effects on metabolic function that might be of benefit in such patients. ALC has been given to HIV patients with symptomatic antiretroviral toxic neuropathy (ATN) in a number of clinical studies.

Diabetic polyneuropathy (DPN) is the most common late complication of diabetes mellitus. Clinical trials utilising ALC have shown beneficial effects on nerve conduction slowing, neuropathic pain, axonal degenerative changes and nerve fibre regeneration, despite relatively late initiation in the natural history of DPN. Owing to the good safety profile of ALC, early initiation of ALC therapy would be justified, with potentially greater benefits.

Soy isoflavones and L-carnitine stimulate carnitine palmitoyl transferase 1A and a cofactor for beta-oxidation of fatty acids, respectively, thus enhancing fatty acid oxidation. These results suggest that these compounds may be effective in controlling obesity.

Fatigue is the most commonly reported symptom in patients with cancer, with a prevalence of over 60% reported in the majority of studies. Clinical trials that assessed pharmacologic agents for the treatment of cancer related fatigue include ALC. Nucleoside reverse transcriptase inhibitors disrupt neuronal mitochondrial DNA synthesis, resulting in antiretroviral toxic neuropathy (ATN). ALC enhances neurotrophic support of sensory neurones, potentially providing symptom relief and nerve regeneration. ALC, administered twice a day intramuscularly to HIV-1-infected patients with symptomatic ATN, significantly reduced weekly mean pain ratings compared with a placebo. Oral ALC even improved symptoms. Intramuscular and oral ALC was generally safe and well tolerated. Carnitine deficiency is among the many metabolic disturbances that may contribute to fatigue in patients with cancer. Administration of ALC may hold promise as a treatment for this common symptom as shown in Phase I/II trials to assess the safety and tolerability of exogenous ALC and clarify the safe dose range associated with symptom effects for future controlled trials. Of the 38 patients screened for carnitine levels, 29 were deficient (76%). The highest dose used in these studies was 3000 mg/day. No patient experienced significant side effects and no toxicities were noted. These findings suggest that ALC may be safely administered at doses up to 3000 mg, where positive effects may be more likely to occur. Treatments for cancer-related fatigue with an aim to develop directions for future research in large, randomized clinical trials should be pursued.

Supplementation with ALC does not impair the ability of epirubicin to kill breast cancer cells. These results suggest that supplementation with ALC in patients undergoing epirubicin treatment could be safely used to reduce associated cardiotoxicities without fear that the efficacy of chemotherapy is jeopardized.

Recent publications have linked oxidative stress to a variety of upper gastrointestinal insults. ALC prevents the oxidative stress response and hold great promise for antioxidant compounds that are safe, efficacious, and inexpensive.

Lack of sufficient levels of ALC is among the postulated causes of fatigue, a highly prevalent symptom in the multiple sclerosis (MS) population, which has a serious impact on patients' quality of life. Deficiency of carnitine may play a role by reducing energy production through fatty acid oxidation and numerous MS therapies can induce fatigue syndrome. For 63% of patients treated with immunosuppressive or immunomodulatory therapies, oral ALC decreased fatigue intensity, especially in patients treated with cyclophosphamide and interferon beta.

Lipoic Acid (Alpha-Lipoic Acid (ALA))

The antioxidant alpha-lipoic acid (ALA) is a naturally occurring compound that has been shown to posses promising anti-cancer activity because of its ability to preferentially induce apoptosis and inhibit proliferation of cancer cells relative to normal cells.

Studies have shown ALA at a dosage of 300 mg/day and N-acetyl cysteine at 1800 mg/day demonstrated that long-term combined maintenance therapy with rIL-2+medroxyprogesterone acetate (MPA)+antioxidant agents is feasible, has a very low toxicity, and results in the improvement of clinical outcome. The antioxidants N-acetylcysteine and ALA markedly reduced the effect of the hormone on tumor necrosis factor-induced caspase activation, attesting to the involvement of reactive oxygen species (ROS) in the crosstalk between the hormone and the cytokine. Researchers have also tested the ability of different antioxidant agents, used alone or in combination, to reduce the reactive oxygen species (ROS) levels and to increase the glutathione peroxidase (GPx) activity. One such study included fifty-six advanced stage cancer patients who were mainly stage III (12.5%) and stage IV (82.1%). Single antioxidants were effective in reducing the ROS levels.

The results of ALA use in human cancer chemotherapy and as a chemopreventive agent by a significant inhibition of the formation of the depurinating adducts have recently been reviewed in light of ALA future inclusion into chemotherapeutic protocols.

One study showed ALA induced reactive oxygen species (ROS) generation and a concomitant increase in apoptosis of human lung epithelial cancer H460 cells. Apoptosis induced by ALA was found to be mediated through the mitochondrial death pathway, which requires caspase-9 activation. A phase II study with ALA showed efficacy and safety in patients with cancer-related anorexia/cachexia and oxidative stress. An open early-phase II study was designed with 39 patients given 300 mg/day ALA and treatment duration for 4 months. There was an important decrease of proinflammatory cytokines interleukin-6 (IL-6) and tumor necrosis factor-alpha, and a negative relationship worthy of note was only found between LBM and IL-6 changes. As for quality of life evaluation, there was a marked improvement. At the end of the study, 22 of the 39 patients were "responders" or "high responders." They concluded efficacy and safety of the treatment have been shown by the study; therefore a randomized phase III study is warranted.

Menopause is often accompanied by hot flashes and degenerative processes such as arteriosclerosis and atrophic changes of the skin that suggest an acceleration of aging triggered by reduced estrogen levels. Therefore, hormone replacement therapy (HRT) has been considered the most suitable treatment for the above symptoms and processes. However, because of the possible serious side effects of HRT (especially the increased risk of thrombo-embolic accidents and breast cancer) there is a growing demand for alternative treatments of the symptoms and pathological processes associated with menopause. Oxygen stress contributes to menopause and some of its physiopathological effects may be prevented and/or treated by improving the antioxidant defense. Antioxidants, including ALA, have favorable effects on the health and quality of life of women, especially those who cannot be treated with HR or who suffer from high levels of oxygen stress.

Resveratrol

There is mounting evidence in the treatment of a variety of human cancers that resveratrol has preventative or shown anti-cancer activity. Resveratrol is known to have potent anti-inflammatory and antioxidant effects and to inhibit platelet aggregation and the growth of a variety of cancer cells. Its potential chemopreventive and chemotherapeutic activities have been demonstrated in all three stages of carcinogenesis (initiation, promotion, and progression), in both chemically and UVB-induced skin carcinogenesis in mice, as well as in various murine models of human cancers.

Resveratrol has been shown to have positive effects on age longevity, lipid levels and a preventative quality against certain cancers and viral infections. Resveratrol induces apoptosis by up-regulating the expression of Bax, Bak, PUMA, Noxa, Bim, p53, TRAIL, TRAIL-R1/DR4 and TRAIL-R2/DR5 and simultaneously down-regulating the expression of Bcl-2, Bcl-XL, Mcl-1 and survivin. Resveratrol has also been shown to reduce inflammation via inhibition of prostaglandin production, cyclooxygenase-2 activity, and nuclear factor-kappaB activity. Modulation of cell signaling pathway by resveratrol explains its diverse bioactivities related with human health. Resveratrol also potentiates the apoptotic effects of cytokines, chemotherapeutic agents and gamma-radiation. The main target organs of resveratrol are liver and kidney, and it is metabolized by hydroxylation, glucuronidation, sulfation and hydrogenation. As a chemoprevention agent, resveratrol has been shown to inhibit tumor initiation, promotion, and progression. There is growing evidence that resveratrol can prevent or delay the onset of various cancers, heart diseases, ischemic and chemically induced injuries, pathological inflammation and viral infections.

The red grape constituent resveratrol possesses cancer chemopreventive properties in rodents. A phase I study of oral resveratrol (single doses of 0.5, 1, 2.5, or 5 g) was conducted in 10 healthy volunteers per dose level. Consumption of resveratrol did not cause serious adverse events at the highest levels, with peak plasma levels occurring 1.5 h post-dose. Cancer chemopreventive effects of resveratrol in cells in vitro require levels of at least 5 µM.

Resveratrol appears to be a good candidate in chemopreventive or chemotherapeutic strategies and is believed to be a novel weapon for new therapeutic strategies. It is conceivable to design resveratrol-containing emollient or patch, as well as sunscreen and skin-care products for prevention of skin cancer and other conditions, which are believed to be caused by UV radiation.

Resveratrol is a phytoalexin produced naturally by several plants when under attack by pathogens such as bacteria or fungi. Resveratrol (3,4',5-trihydroxystilbene) is found in various plants, including grapes, berries and peanuts. It is also present in wines, especially red wines. During the last years, it has been the focus of numerous in vitro and in vivo studies investigating its biological attributes, which include mainly antioxidant and anti-inflammatory activities, anti-platelet aggregation effect, and chemoprevention.

In fact, recently, it has been demonstrated that the stilbene blocks the multistep process of carcinogenesis at various stages: tumor initiation, promotion and progression. More recent results provide interesting insights into the effect of this compound on the life span of yeasts and flies, implicating the potential of resveratrol as an anti-aging agent in treating age-related human diseases. Resveratrol has the potential to act as an estrogen agonist or antagonist depending on such factors as cell type, estrogen receptor isoform (ER alpha or ER beta), and the presence of endogenous estrogens.

In summary, the search for novel and effective cancer chemopreventive agents has led to the identification of various naturally occurring compounds one of which is resveratrol (trans-3,4',5-trihydroxystilbene), a phytoalexin derived from the skin of grapes and other fruits. Resveratrol is known to have potent anti-inflammatory and antioxidant effects and to inhibit platelet aggregation and the growth of a variety of cancer cells. Its potential chemopreventive and chemotherapeutic activities have been demonstrated in all three stages of carcinogenesis (initiation, promotion, and progression), in both chemically and UVB-induced skin carcinogenesis in mice, as well as in various murine models of human cancers. Evidence from numerous in vitro and in vivo studies has confirmed its ability to modulate various targets and signaling pathways.

Vitamin C

Vitamin C is water soluble and antioxidant vitamin and cannot be stored in the body. It is excreted from the body regularly, so you have to supply it regularly to the body. It is used for proper functioning of human body. It is also known as ascorbic acid. Ascorbic acid is an antioxidant which helps in protecting the body against pollutants. Ascorbic acid helps in promoting healthy cell development, normal tissue growth and repair such as healing injuries and burns, and helps in absorption of calcium.

The main function of vitamin C is that it helps in the synthesis of collagen. Collagen is an important component of ligaments, blood vessels, bone and tendons. It is found throughout the body, present in cartilage and connective tissues and is used to separate skeletal and smooth muscle cells. Vitamin C is useful for healthy gums to help in protecting against infections. It also strengthens many parts of your body such as blood vessels and muscles.

Scurvy is the main disease that is caused by vitamin C deficiency. It is characterized by loose teeth, anemia, poor healing, easy bruising and fragility of blood vessels. The other deficiencies include dry and splitting hair, bleeding gums, nose bleeds, swollen and painful joints, rough and dry skin. The symptoms of vitamin C deficiency include weight loss, irritability, fatigue, depression and weakness. Low levels of it cause gall bladder disease, atherosclerosis, hypertension, stroke and cancer.

Additional Optional Components to the Formulation

In addition to the components discussed above, arabinoxylan and peperine may be added.

Arabinoxylan

The role of dietary fiber in the prevention of colon cancer rate is still not completely understood despite numerous investigations that stemmed from Burkitt's pioneering studies in 1971 concerning the importance of dietary fibers in preventing colon cancer in humans. Epidemiological studies suggest an inverse relationship between the intake of dietary fiber, particularly fiber from cereal grains, and colon cancer risk. Animal model assays have demonstrated that the protective effects of dietary fiber on colon cancer development depend on the nature and source of the fiber. Wheat bran (WB) appears to inhibit colon tumor genesis more consistently than do oat bran or corn bran. One study demonstrated for the first time that the lipid fraction of wheat bran has strong colon tumor inhibitor properties. Wheat bran has been shown to be the best diluter of colonic contents.

The Wheat Bran Fiber (WBF) trial is a Phase III clinical trial designed to assess the effect of a WBF intervention for 3 years on the recurrence of adenomatous polyps. It is estimated that without preventive actions, about 6% of Americans will develop colorectal cancer sometime over their lifetime. The majority of colorectal cancers arise from the premalignant lesion, the adenomatous polyp, and removal of these lesions has been shown to substantially reduce the subsequent risk for colorectal cancer. An abundant amount of research has been devoted to the study of diet in the etiology of this malignancy. Wheat bran protects against colon cancer, but the mechanism(s) is not known. Possible mechanisms for wheat bran's antineoplastic effects are butyrate's enhancement of apoptosis and control of proliferation soon after carcinogen-induced DNA damage to colon tissue. Apoptosis recently was reported to be a better predictor of tumor outcome than proliferation in induced carcinogenesis models. The elimination of damaged cells during tumor initiation would limit the number of aberrant crypts and tumors later in life. Control of the zone of proliferation to the lower two-thirds of the crypt would decrease the number of cells lining the crypt, normalize the luminal surface, and thus limit the number of aberrant crypt foci (ACF). Poorly fermented fibers, such as wheat bran, cellulose and lignin, are protective against colon cancer. Wheat bran has shown increases in cell proliferation, differences in the location of greatest butyrate concentration and alterations in luminal pH as a possibility for an explanation of differences between positive and negative effects between fermented and poorly fermented fibers. The protective value of a fiber has often been linked to the production of butyrate and especially the concentration of butyrate in the distal colon. Butyrate has long been the focal point of studies of colon physiology and pathophysiology, primarily because of its importance as the preferred source of metabolic fuel for the colonocyte.

A group of rats consuming diets containing oat bran at a concentration of 6 g oat bran per 100 g body weight had greater body weights, produced larger concentrations of short-chain fatty acids, including butyrate, in both the proximal and distal colon, had more acidic luminal pH values, but also had a significantly larger number of animals develop colon tumors than their wheat bran counterparts. There is further evidence that dietary supplements of wheat bran may protect against colon cancer. The effects of supplementing the diet of female Wistar rats with 10% wheat bran on the disposition and metabolism of the dietary carcinogen 2-amino-3-methylimidazo[4,5-f]quinoline (IQ) was studied. One of the most marked effects of wheat bran was apparently to significantly retard the metabolism of IQ in the plasma.

In summary, supplementing the diet of both animals and humans with various dietary fiber sources is known to have a potential ability to protect against the development of cancer. Numerous animal studies indicate that supplementing one's diet with wheat bran protects against colon cancer.

In order to find the active ingredients of bran fiber, MGN-3/Biobran, modified arabinoxylan rice bran, has been shown to be a potent biological response modifier. Results have revealed that MGN-3, in a dose dependent manner (1, 10, 100 µg/ml), significantly induced high levels of production of cytokines: TNF-alpha; and IL-6. In addition, MGN-3 significantly increased nitric oxide (NO) production. This data demonstrates that MGN-3 is a potent inducer of phagocytic function by macrophage, and suggests that MGN-3 is a useful agent for fighting microbial infection.

Arabinoxylan, which is a complex polysaccharide in the cereal cell wall, has been investigated as a biological response modifier. The leading manufacturer of this type of hemicellulose food supplement is Daiwa Pharmaceutical in Japan, which has a unique and patented process in which rice bran is broken down (partially hydrolyzed) using Shitake mushroom enzymes (lentius edodes mycelia extract) to make a unique and natural blend of hemicelluloses, the principal ingredient of which is the arabinoxylan compound or b-1,4 xylophyronase hemicellulose. The research was performed to release and activate arabinoxylan from rice bran by using a combined process of extrusion and commercial hemicellulase. The results showed that extrusion and subsequent enzyme treatment was an industrially applicable tool for effective release of arabinoxylan with high yield and purity.

The non-cellulostic polysaccharides present in cereals (2-8% w/w) are mostly arabinoxylans, (1→3), (1→4)-beta-glucans, pectins, and arabinogalactins. Of these, the arabinoxylans are known to absorb large amounts of water. Nutritionally, they are classified under "unavailable carbohydrates" (dietary fiber) and are known to have beneficial effects in alleviating disease symptoms such as diabetes, atherosclerosis, and colon cancer.

Peperine

Peperine is an alkaloid found in peppercorn spikes. Peperine is also found in black pepper and similar plants. Peperine is said to increase thermogenesis—the process of generating energy in cells—and may increase access to the bloodstream by improving the bioavailability of other nutritive substances Peperine may be helpful in reducing inflammation and pain, improving digestion, and relieving asthma. Peperine has been used for various illnesses, including the treatment of stomach aches, malaria, headaches, fever, and weight loss.

DETAILED DESCRIPTION

The present disclosure provides for a scientific formulation useful in the treatment and prevention of human and animal diseases. All components of the formulation may be provide in one dosage and administered in many different ways currently known in the art. According to the present disclosure, a biologically effective amount of each of the components of the formulation is administered to patients in pill (or capsule) form via multiple different and identifiable pills. In other embodiments, the formulation may be provided in an oral dosage form selected from the group consisting of a chewable tablet, a quick dissolve tablet, an effervescent tablet, a hard gelatin capsule, a soft gelatin capsule, a reconstitutable powder, a suspension, an elixor, a caplet, a health bar, a liquid, a food or combinations thereof. Additionally, the formulation may also be administered sublingually, topically, by intravascular injection, by intramuscular injection, by subcutaneous injection. For purposes of this disclosure, a "biologically effective amount" is used to describe an amount effective to cause identifiable, quantitative results by any degree. In one embodiment, a biologically effective amount refers to the amount identified on Table 1, per patient per day.

In one embodiment, the compounds of the formulation are segregated into three different pill types—Antiangiogenesis, Vitamin, and Antioxidant—as identified in Table 1. The Antiangiogenesis pill includes various amounts of the compounds Curcumin, Genistein, Squalamine and Vitamin E in the ranges identified in Table 1. The Vitamin pill includes various amounts of the compounds N-Acetyl-Cysteine, Methylselenocysteine, Zinc Gluconate, B Complex, and Lentinen. The Antioxidant pill includes Coenzyme Q10, Acetyl-L-Camitine, Lipoic Acid, Resveratrol, and Vitamin C. However, the components in the formulation may be combined in many different pill forms without departing from the scope of the disclosure contained herein. Furthermore, Arabinoxylan and/or peperine may be added to either of the three pill formulations.

For Curcumin, ingestion in the range of generally about 1500 mg to generally about 3000 mg per day is effective. For Genistein, ingestion in the range of generally about 24 mg to generally about 68 mg per day is effective. For Squalamine, ingestion in the range of generally about 150 mg to generally about 300 mg per day is effective. For Vitamin E, ingestion in the range of generally about 200 mg to generally about 400 mg per day is effective.

For N-Acetyl-Cysteine, ingestion in the range of generally about 2000 mg to generally about 5000 mg per day is effective. For Methylselenocysteine, ingestion in the range of generally about 0.2 mg to generally about 0.6 mg per day is effective. For Zinc Gluconate, ingestion in the range of generally about 200 mg to generally about 300 mg per day is effective. For B Complex, ingestion in the range of generally about 200 mg to generally about 700 mg per day is effective. For Lentinen, ingestion in the range of generally about 111 mg to generally about 300 mg per day is effective.

For Coenzyme Q10, ingestion in the range of generally about 100 mg to generally about 450 mg per day is effective. For Acetyl-L-Carnitine, ingestion in the range of generally about 1000 mg to generally about 2000 mg per day is effective. For Lipoic Acid, ingestion in the range of generally about 150 mg to generally about 300 mg per day is effective. For Resveratrol, ingestion in the range of generally about 500 mg to generally about 1500 mg per day is effective. For Vitamin C, ingestion in the range of generally about 100 mg to generally about 3000 mg per day is effective.

For Arabinoxylan, ingestion in the range of generally about 50 mg to generally about 250 mg per day is effective. Finally, peperine helps the formulation components gain access to the bloodstream faster with smaller dosages. For peperine, ingestion in the range of generally about 5 mg to generally about 45 mg per day is effective.

In another embodiment, the compounds of the formulation are segregated into four different pill types—Antiangiogenesis, Vitamin/Element, Antioxidant and Enhanced NAC. The Antiangiogenesis pill includes various amounts of the compounds Curcumin, Genistein, Vitamin E and Peperine in the ranges identified in Table 1. The Vitamin/Element pill includes various amounts of the compounds Selenium (Methylselenocysteine), Zinc Gluconate, B Complex, and Lentinen in the ranges identified in Table 1. The Antioxidant pill includes Coenzyme Q10, Acetyl-L-Carnitine, Lipoic Acid, Resveratrol, and Vitamin C in the ranges identified in Table 1. The enhanced NAC pill contains N-Acetyl-Cysteine in the ranges identified in Table 1.

This invention may be provided in other specific forms and embodiments without departing from the essential characteristics as described herein. The embodiments described above are to be considered in all aspects as illustrative only and not restrictive in any manner.

As described above, the present invention comprises a formulation for the treatment of animal and human diseases. While particular embodiments of the invention have been described, it will be understood, however, that the disclosure is not limited thereto, since modifications may be made by those skilled in the art, particularly in light of the foregoing teachings. It is, therefore, contemplated that the claims cover any such modifications that incorporate those features or those improvements that embody the spirit and scope of the present invention.

TABLE 1

| PILL TYPE | PER DAY (mg) | SINGLE PILL (mg) | RANGE |
|---|---|---|---|
| ANTIANGIOGENESIS | | | |
| Curcumin | 2000 | 667 | (500-3000 mg) |
| Genistein | 48 | 16 | (10-68 mg) |
| Squalamine | 300 | 100 | (50-300 mg) |
| Vitamin E | 294 | 98 | (50-400 mg) |
| VITAMIN | | | |
| N-Acetyl-Cysteine | 2500 | 833 | (500-5000 mg) |
| Methylselenocysteine | 0.4 | 0.13 | (0.2-0.6 mg) |
| Zinc Gluconate | 250 | 83.3 | (200-300 mg) |
| B Complex | 500 | 167 | (100-700 mg) |
| Lentinen | 333 | 111 | (50-400 mg) |
| ANTIOXIDANT | | | |
| CoQ10 | 150 | 50 | (20-450 mg) |
| Acetyl-L-Carnitine | 1000 | 333 | (300-2000 mg) |
| Lipoic Acid | 300 | 100 | (50-400 mg) |
| Resveratrol | 500 | 167 | (100-1500 mg) |
| Vitamin C | 1500 | 500 | (100-3000 mg) |
| Optional | | | |
| Arabinoxylan | 150 | 50 | (25-400 mg) |
| Peperine | 30 | 10 | (5-45 mg) |

What is claimed is:

1. A method for treating colon cancer, prostate cancer, lung cancer and/or ovarian cancer, which consists of orally administering to a patient in need thereof a composition consisting of:
    about 1500 mg to about 3000 mg of Curcumin, about 24 mg to about 68 mg of Genistein; about 150 mg to about 300 mg of Squalamine; about 200 mg to about 400 mg of Vitamin E; about 2000 mg to about 5000 mg of N-Acetyl-Cysteine; about 0.2 mg to about 0.6 mg of Methylselenocysteine; about 200 mg to about 300 mg of Zinc Gluconate;
    about 200 mg to about 700 mg of Vitamin B Complex; about 111 mg to about 300 mg of Lentinen; about 100 mg to about 450 mg of Coenzyme Q10; about 1000 mg to about 2000 mg of Acetyl-L-Carnitine; about 150 mg to about 300 mg of Lipoic Acid; about 500 mg to about 1500 mg of Resveratrol; about 100 mg to about 3000 mg of Vitamin C; and about 5 mg to about 45 mg of Peperine.

2. The method of claim 1, wherein said composition is an oral dosage form selected from the group consisting of a chewable tablet, a quick dissolve tablet, an effervescent tablet, a hard gelatin capsule, a soft gelatin capsule, a reconstitutable powder, a suspension, an elixir, a caplet, a health bar, a liquid, a food and combinations thereof.

3. The method of claim 1, wherein said composition is an oral dosage form is selected from the group consisting of immediate release, extended release, pulse release, delayed release, timed release, variable release, controlled release and combinations thereof.

4. The method of claim 1, wherein said composition is administered once during a twenty-four hour period of time.

5. The method of claim 1, wherein said composition is administered more than once during a twenty-four hour period of time.

6. A method for treating colon cancer, prostate cancer, lung cancer and/or ovarian cancer, which consists of
   a. orally administering to a patient in need thereof a first composition consisting of about 1500 mg to about 3000 mg of Curcumin, about 24 mg to about 68 mg of Genistein; about 150 mg to about 300 mg of Squalamine; and about 200 mg to about 400 mg of Vitamin E;
   b. orally administering to the patient a second composition consisting of about 2000 mg to about 5000 mg of N-Acetyl-Cysteine; about 0.2 mg to about 0.6 mg of Methylselenocysteine; about 200 mg to about 300 mg of Zinc Gluconate; about 200 mg to about 700 mg of Vitamin B Complex; and about 111 mg to about 300 mg of Lentinen; and
   c. orally administering to the patient a third composition consisting of about 100 mg to about 450 mg of Coenzyme Q10; about 1000 mg to about 2000 mg of Acetyl-L-Carnitine; about 150 mg to about 300 mg of Lipoic Acid; about 500 mg to about 1500 mg of Resveratrol; and about 100 mg to about 3000 mg of Vitamin C.

7. The method of claim 6, wherein said composition is an oral dosage form selected from the group consisting of a chewable tablet, a quick dissolve tablet, an effervescent tablet, a hard gelatin capsule, a soft gelatin capsule, a reconstitutable powder, a suspension, an elixir, a caplet, a health bar, a liquid, a food and combinations thereof.

8. The method of claim 6, wherein said composition is an oral dosage form is selected from the group consisting of immediate release, extended release, pulse release, delayed release, timed release, variable release, controlled release and combinations thereof.

9. The method of claim 6, wherein said first, second and third compositions are administered once during a twenty-four hour period of time.

10. The method of claim 6, wherein said first, second and third compositions are administered more than once during a twenty-four hour period of time.

11. A dietary supplement consisting of about 1500 mg to about 3000 mg of Curcumin, about 24 mg to about 68 mg of Genistein; about 150 mg to about 300 mg of Squalamine; about 200 mg to about 400 mg of Vitamin E; about 2000 mg to about 5000 mg of N-Acetyl-Cysteine; about 0.2 mg to about 0.6 mg of Methylselenocysteine; about 200 mg to about 300 mg of Zinc Gluconate; about 200 mg to about 700 mg of Vitamin B Complex; about 111 mg to about 300 mg of Lentinen; about 100 mg to about 450 mg of Coenzyme Q10; about 1000 mg to about 2000 mg of Acetyl-L-Carnitine; about 150 mg to about 300 mg of Lipoic Acid; about 500 mg to about 1500 mg of Resveratrol; about 100 mg to about 3000 mg of Vitamin C; and about 5 mg to about 45 mg of Peperine.

* * * * *